(12) United States Patent
Abbitt et al.

(10) Patent No.: US 11,814,637 B2
(45) Date of Patent: Nov. 14, 2023

(54) EXPRESSION MODULATING ELEMENTS AND USE THEREOF

(71) Applicant: PIONEER HI-BRED INTERNATIONAL, INC., Johnston, IA (US)

(72) Inventors: Shane E Abbitt, Ankeny, IA (US); Mary J Frank, Des Moines, IA (US); Thomas W Greene, West Des Moines, IA (US); Nandini Krishnamurthy, Grimes, IA (US); Andrew Rupiper, Bondurant, IA (US)

(73) Assignee: PIONEER HI-BRED INTERNATIONAL, INC

( * ) Notice: Subject to any disclaimer, the term of this patent is extended or adjusted under 35 U.S.C. 154(b) by 288 days.

(21) Appl. No.: 16/498,447

(22) PCT Filed: Mar. 30, 2018

(86) PCT No.: PCT/US2018/025446
§ 371 (c)(1),
(2) Date: Sep. 27, 2019

(87) PCT Pub. No.: WO2018/183878
PCT Pub. Date: Oct. 4, 2018

(65) Prior Publication Data
US 2021/0324401 A1 Oct. 21, 2021

Related U.S. Application Data

(60) Provisional application No. 62/479,781, filed on Mar. 31, 2017.

(51) Int. Cl.
*C12N 15/82* (2006.01)

(52) U.S. Cl.
CPC ..... *C12N 15/8274* (2013.01); *C12N 15/8216* (2013.01); *C12N 15/8286* (2013.01)

(58) Field of Classification Search
CPC .................................. C12N 15/8274
USPC ........................................... 800/260
See application file for complete search history.

(56) References Cited

U.S. PATENT DOCUMENTS 5,573,932 A * 11/1996 Ellis ................... C12N 15/67
435/468
2007/0204367 A1 8/2007 Flasinski et al.

FOREIGN PATENT DOCUMENTS

| CN | 102753700 A | 10/2012 |
|---|---|---|
| CN | 103131697 A | 6/2013 |
| CN | 104968790 A | 10/2015 |
| EP | 3 115 457 A1 | 1/2017 |
| WO | 2001/053476 A2 | 7/2001 |
| WO | 2007/098042 A2 | 8/2007 |
| WO | 2013/130813 A1 | 9/2013 |
| WO | 2014/151749 A1 | 9/2014 |

OTHER PUBLICATIONS

Jores et al., The Plant Cell (32):2120-2131 (Year: 2020).*
Database Geneseq Database Accession No. AAH42715, "A promoter element of transcription binding site", XP002781486, Oct. 1, 2002 (Oct. 1, 2002).
Ellis, J. G.; et al.: "The ocs element: a 16 base pair palindrome essential for activity of the octopine synthase enhancer", The EMBO Journal, Nov. 1, 1987 (Nov. 1, 1987), vol. 6, No. 11, pp. 3203-3208.
Liu, Shijuan; et al.: "Effects of copy number of an octopine synthase enhancer element and its distance from the TATA box on heterologous expression in transgenic tobacco", Acta Physiologiae Plantrum, Feb. 19, 2009 (Feb. 19, 2009), vol. 31, No. 4, pp. 705-710.
Singh, Karambir; et al.: "Saturation mutagenesis of the octopine synthase enhancer: Correlation of mutant phenotypes with binding of a nuclear protein factor", PNAS, May 1, 1989 (May 1, 1989), vol. 86, pp. 3733-3737.
Sawant et al., "Designing of an artificial expression cassette for the high-level expression of transgenes in plants", Theor Appl Genet (2001) 102:635-644.
International Search Report and Written Opinion for International Application PCT/US2018/025446, dated Sep. 12, 2018.
EP Examination Report for EP Application No. 18 720 692.5, dated Aug. 20, 2020.
Third Party Observation by Susen Herrmann for EP Application No. 18 720 692, "Expression Modulating Elements and Use Thereof," Publication No. EP3601579, Published Feb. 5, 2020 (Filed Mar. 30, 2018).
Ellis, J.G.; et al.: "The ocs element: a 16 base pair palindrome essential for activity of the octopine synthase enhancer," The EMBO Journal, 1987, vol. 6, No. 11, pp. 3203-3208.
Lam, Eric; et al.: "Site-specific mutations alter in vitro factor binding and change promoter expression patterns in transgenic plants," Proc. Natl. Acad. Sci. USA, Oct. 1989, vol. 86, pp. 7890-7894.
International Preliminary Report on Patentability for International Application No. PCT/US2018/025446, dated Oct. 10, 2019, 11 Pages.

* cited by examiner

*Primary Examiner* — Li Zheng

(57) ABSTRACT

The disclosure relates to gene expression modulation elements from plants and their use in modulating the expression of one or more heterologous nucleic acid fragments in plants. The disclosure further discloses compositions, polynucleotide constructs, transformed host cells, plants and seeds containing the expression modulating elements, and methods for preparing and using the same.

14 Claims, 5 Drawing Sheets

Figure 1:
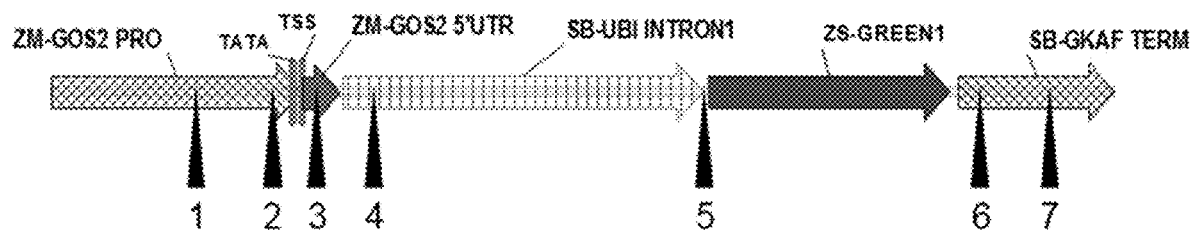

Specification includes a Sequence Listing.

A.

B.

SEQUENCE LISTING

```
<160> NUMBER OF SEQ ID NOS: 68

<210> SEQ ID NO 1
<211> LENGTH: 17
<212> TYPE: DNA
<213> ORGANISM: Zea mays

<400> SEQUENCE: 1
tgacgtaagg tatgacg                                                  17

<210> SEQ ID NO 2
<211> LENGTH: 14
<212> TYPE: DNA
<213> ORGANISM: Zea mays

<400> SEQUENCE: 2
cgtaaggtat gacg                                                     14

<210> SEQ ID NO 3
<211> LENGTH: 22
<212> TYPE: DNA
<213> ORGANISM: Zea mays

<400> SEQUENCE: 3
aacaacgtaa gcgcttacgc ac                                            22

<210> SEQ ID NO 4
<211> LENGTH: 16
<212> TYPE: DNA
<213> ORGANISM: Zea mays

<400> SEQUENCE: 4
acgtaagcgc ttacgc                                                   16

<210> SEQ ID NO 5
<211> LENGTH: 14
<212> TYPE: DNA
<213> ORGANISM: Zea mays
```

<400> SEQUENCE: 5
cgtaagcgct tacg                                                     14

<210> SEQ ID NO 6
<211> LENGTH: 14
<212> TYPE: DNA
<213> ORGANISM: Zea mays

<400> SEQUENCE: 6
cgtaaacaaa tacg                                                     14

<210> SEQ ID NO 7
<211> LENGTH: 14
<212> TYPE: DNA
<213> ORGANISM: Zea mays

<400> SEQUENCE: 7
cgtaaacgct tacg                                                     14

<210> SEQ ID NO 8
<211> LENGTH: 17
<212> TYPE: DNA
<213> ORGANISM: Zea mays

<400> SEQUENCE: 8
tgacgtatgg tatgacg                                                  17

<210> SEQ ID NO 9
<211> LENGTH: 14
<212> TYPE: DNA
<213> ORGANISM: Zea mays

<400> SEQUENCE: 9
cgtaaggtct tacg                                                     14

<210> SEQ ID NO 10
<211> LENGTH: 14
<212> TYPE: DNA
<213> ORGANISM: Zea mays

<400> SEQUENCE: 10
cgtaagtcct tacg                                                     14

<210> SEQ ID NO 11
<211> LENGTH: 14
<212> TYPE: DNA
<213> ORGANISM: Zea mays

<400> SEQUENCE: 11
cgtaagtgct tacg                                                     14

<210> SEQ ID NO 12
<211> LENGTH: 14
<212> TYPE: DNA
<213> ORGANISM: Zea mays

<400> SEQUENCE: 12
cgtaaggcct tacg                                                     14

<210> SEQ ID NO 13
<211> LENGTH: 14
<212> TYPE: DNA

```
<213> ORGANISM: Zea mays

<400> SEQUENCE: 13
cgtaagacct tacg                                                        14

<210> SEQ ID NO 14
<211> LENGTH: 14
<212> TYPE: DNA
<213> ORGANISM: Zea mays

<400> SEQUENCE: 14
cgtaaggact tacg                                                        14

<210> SEQ ID NO 15
<211> LENGTH: 14
<212> TYPE: DNA
<213> ORGANISM: Zea mays

<400> SEQUENCE: 15
cgtaagcact tacg                                                        14

<210> SEQ ID NO 16
<211> LENGTH: 14
<212> TYPE: DNA
<213> ORGANISM: Zea mays

<400> SEQUENCE: 16
cgtaagggct tacg                                                        14

<210> SEQ ID NO 17
<211> LENGTH: 14
<212> TYPE: DNA
<213> ORGANISM: Zea mays

<400> SEQUENCE: 17
cgtaagccct tacg                                                        14

<210> SEQ ID NO 18
<211> LENGTH: 14
<212> TYPE: DNA
<213> ORGANISM: Zea mays

<400> SEQUENCE: 18
cgtaagtact tacg                                                        14

<210> SEQ ID NO 19
<211> LENGTH: 14
<212> TYPE: DNA
<213> ORGANISM: Zea mays

<400> SEQUENCE: 19
cgtaagatct tacg                                                        14

<210> SEQ ID NO 20
<211> LENGTH: 16
<212> TYPE: DNA
<213> ORGANISM: Zea mays

<400> SEQUENCE: 20
gcgtaagcgc ttacgc                                                      16

<210> SEQ ID NO 21
<211> LENGTH: 16
```

<212> TYPE: DNA
<213> ORGANISM: Zea mays

<400> SEQUENCE: 21
aagtaagcgc ttactt                                              16

<210> SEQ ID NO 22
<211> LENGTH: 16
<212> TYPE: DNA
<213> ORGANISM: Zea mays

<400> SEQUENCE: 22
acttaagcgc ttaagt                                              16

<210> SEQ ID NO 23
<211> LENGTH: 16
<212> TYPE: DNA
<213> ORGANISM: Zea mays

<400> SEQUENCE: 23
acggaagcgc ttccgt                                              16

<210> SEQ ID NO 24
<211> LENGTH: 16
<212> TYPE: DNA
<213> ORGANISM: Zea mays

<400> SEQUENCE: 24
acgtgagcgc tcacgt                                              16

<210> SEQ ID NO 25
<211> LENGTH: 16
<212> TYPE: DNA
<213> ORGANISM: Zea mays

<400> SEQUENCE: 25
acgtaggcgc ctacgt                                              16

<210> SEQ ID NO 26
<211> LENGTH: 16
<212> TYPE: DNA
<213> ORGANISM: Zea mays

<400> SEQUENCE: 26
acgtaatcga ttacgt                                              16

<210> SEQ ID NO 27
<211> LENGTH: 16
<212> TYPE: DNA
<213> ORGANISM: Zea mays

<400> SEQUENCE: 27
gatcggtata ccgatc                                              16

<210> SEQ ID NO 28
<211> LENGTH: 10
<212> TYPE: DNA
<213> ORGANISM: Zea mays
<220> FEATURE:
<221> NAME/KEY: misc_feature
<222> LOCATION: (9)..(10)
<223> OTHER INFORMATION: n is a, c, g, or t

<400> SEQUENCE: 28

```
gcttacgtnn                                                          10

<210> SEQ ID NO 29
<211> LENGTH: 10
<212> TYPE: DNA
<213> ORGANISM: Zea mays
<220> FEATURE:
<221> NAME/KEY: misc_feature
<222> LOCATION: (9)..(10)
<223> OTHER INFORMATION: n is a, c, g, or t

<400> SEQUENCE: 29 acgtaagcnn                                                          10

<210> SEQ ID NO 30
<211> LENGTH: 16
<212> TYPE: DNA
<213> ORGANISM: Zea mays

<400> SEQUENCE: 30
acgtaagcgc ttacgt                                                   16

<210> SEQ ID NO 31
<211> LENGTH: 20
<212> TYPE: DNA
<213> ORGANISM: Zea mays

<400> SEQUENCE: 31
acaacgtaag cgcttacgca                                               20

<210> SEQ ID NO 32
<211> LENGTH: 18
<212> TYPE: DNA
<213> ORGANISM: Zea mays

<400> SEQUENCE: 32
caacgtaagc gcttacgc                                                 18

<210> SEQ ID NO 33
<211> LENGTH: 15
<212> TYPE: DNA
<213> ORGANISM: Zea mays

<400> SEQUENCE: 33
acgtaagcgc ttacg                                                    15

<210> SEQ ID NO 34
<211> LENGTH: 15
<212> TYPE: DNA
<213> ORGANISM: Zea mays

<400> SEQUENCE: 34
cgtaagcgct tacgc                                                    15

<210> SEQ ID NO 35
<211> LENGTH: 13
<212> TYPE: DNA
<213> ORGANISM: Zea mays

<400> SEQUENCE: 35
cgtaagcgct tac                                                      13

<210> SEQ ID NO 36
<211> LENGTH: 13
```

```
<212> TYPE: DNA
<213> ORGANISM: Zea mays

<400> SEQUENCE: 36
gtaagcgctt acg                                                        13

<210> SEQ ID NO 37
<211> LENGTH: 10
<212> TYPE: DNA
<213> ORGANISM: Zea mays

<400> SEQUENCE: 37
taagcgctta                                                            10

<210> SEQ ID NO 38
<211> LENGTH: 10
<212> TYPE: DNA
<213> ORGANISM: Zea mays
<220> FEATURE:
<221> NAME/KEY: misc_feature
<222> LOCATION: (9)..(10)
<223> OTHER INFORMATION: n is a, c, g, or t

<400> SEQUENCE: 38 aagcgcttnn                                                            10

<210> SEQ ID NO 39
<211> LENGTH: 21
<212> TYPE: DNA
<213> ORGANISM: Zea mays

<400> SEQUENCE: 39
ctgacgtaag ggatgacgca c                                               21

<210> SEQ ID NO 40
<211> LENGTH: 16
<212> TYPE: DNA
<213> ORGANISM: Zea mays

<400> SEQUENCE: 40
gacgtaaggt atgacg                                                     16

<210> SEQ ID NO 41
<211> LENGTH: 15
<212> TYPE: DNA
<213> ORGANISM: Zea mays

<400> SEQUENCE: 41
acgtaaggta tgacg                                                      15

<210> SEQ ID NO 42
<211> LENGTH: 13
<212> TYPE: DNA
<213> ORGANISM: Zea mays

<400> SEQUENCE: 42
gtaaggtatg acg                                                        13

<210> SEQ ID NO 43
<211> LENGTH: 12
<212> TYPE: DNA
<213> ORGANISM: Zea mays

<400> SEQUENCE: 43
```
taaggtatga cg                                                              12

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
ctgacgtaag cgcttacgta c                                                    21

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ctgacgtaag cgctgacgta c                                                    21

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
ctgacgtaag cgctgacgca c                                                    21

<210> SEQ ID NO 47
<211> LENGTH: 16
<212> TYPE: DNA
<213> ORGANISM: Artificial Sequence
<220> FEATURE:
<223> OTHER INFORMATION: Synthetic

<400> SEQUENCE: 47
acgtaagcga ttacgt                                                          16

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
ctgacgtaag cgattacgca c                                                    21

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
ctgacgtaag cgattacgta c                                                    21

<210> SEQ ID NO 50
<211> LENGTH: 21
<212> TYPE: DNA
<213> ORGANISM: Artificial Sequence

```
<220> FEATURE:
<223> OTHER INFORMATION: Synthetic

<400> SEQUENCE: 50
ctgacgtaag ggattacgta c                                              21

<210> SEQ ID NO 51
<211> LENGTH: 22
<212> TYPE: DNA
<213> ORGANISM: Artificial Sequence
<220> FEATURE:
<223> OTHER INFORMATION: Synthetic

<400> SEQUENCE: 51
aatgacgtaa gcgcttacgc ac                                             22

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
aatgacgtaa gcgctgacgc ac                                             22

<210> SEQ ID NO 53
<211> LENGTH: 12
<212> TYPE: DNA
<213> ORGANISM: Artificial Sequence
<220> FEATURE:
<223> OTHER INFORMATION: Enhancer

<400> SEQUENCE: 53
cgtaaggtat ga                                                        12

<210> SEQ ID NO 54
<211> LENGTH: 12
<212> TYPE: DNA
<213> ORGANISM: Artificial Sequence
<220> FEATURE:
<223> OTHER INFORMATION: ENHANCER

<400> SEQUENCE: 54
gtaaggtatg ac                                                        12

<210> SEQ ID NO 55
<211> LENGTH: 12
<212> TYPE: DNA
<213> ORGANISM: Artificial Sequence
<220> FEATURE:
<223> OTHER INFORMATION: ENHANCER

<400> SEQUENCE: 55
gacgtaaggt at                                                        12

<210> SEQ ID NO 56
<211> LENGTH: 13
<212> TYPE: DNA
<213> ORGANISM: Artificial Sequence
<220> FEATURE:
<223> OTHER INFORMATION: ENHANCER

<400> SEQUENCE: 56
acgtaaggta tga                                                       13
```

```
<210> SEQ ID NO 57
<211> LENGTH: 13
<212> TYPE: DNA
<213> ORGANISM: Artificial Sequence
<220> FEATURE:
<223> OTHER INFORMATION: ENHANCER

<400> SEQUENCE: 57
cgtaaggtat gac                                                          13

<210> SEQ ID NO 58
<211> LENGTH: 13
<212> TYPE: DNA
<213> ORGANISM: Artificial Sequence
<220> FEATURE:
<223> OTHER INFORMATION: ENHANCER

<400> SEQUENCE: 58
gacgtaaggt atg                                                          13

<210> SEQ ID NO 59
<211> LENGTH: 14
<212> TYPE: DNA
<213> ORGANISM: Artificial Sequence
<220> FEATURE:
<223> OTHER INFORMATION: ENHANCER

<400> SEQUENCE: 59
acgtaaggta tgac                                                         14

<210> SEQ ID NO 60
<211> LENGTH: 14
<212> TYPE: DNA
<213> ORGANISM: Artificial Sequence
<220> FEATURE:
<223> OTHER INFORMATION: ENHANCER

<400> SEQUENCE: 60
gacgtaaggt atga                                                         14

<210> SEQ ID NO 61
<211> LENGTH: 15
<212> TYPE: DNA
<213> ORGANISM: Artificial Sequence
<220> FEATURE:
<223> OTHER INFORMATION: ENHANCER

<400> SEQUENCE: 61
gacgtaaggt atgac                                                        15

<210> SEQ ID NO 62
<211> LENGTH: 11
<212> TYPE: DNA
<213> ORGANISM: Artificial Sequence
<220> FEATURE:
<223> OTHER INFORMATION: ENHANCER

<400> SEQUENCE: 62
taagcgctta c                                                            11

<210> SEQ ID NO 63
<211> LENGTH: 12
<212> TYPE: DNA
<213> ORGANISM: Artificial Sequence
<220> FEATURE:
<223> OTHER INFORMATION: ENHANCER
```

```
<400> SEQUENCE: 63
gtaagcgctt ac                                                              12

<210> SEQ ID NO 64
<211> LENGTH: 12
<212> TYPE: DNA
<213> ORGANISM: Artificial Sequence
<220> FEATURE:
<223> OTHER INFORMATION: ENHANCER

<400> SEQUENCE: 64
taagcgctta cg                                                              12

<210> SEQ ID NO 65
<211> LENGTH: 14
<212> TYPE: DNA
<213> ORGANISM: Artificial Sequence
<220> FEATURE:
<223> OTHER INFORMATION: ENHANCER

<400> SEQUENCE: 65
gtaagcgctt acgc                                                            14

<210> SEQ ID NO 66
<211> LENGTH: 16
<212> TYPE: DNA
<213> ORGANISM: Artificial Sequence
<220> FEATURE:
<223> OTHER INFORMATION: ENHANCER

<400> SEQUENCE: 66
aacgtaagcg cttacg                                                          16

<210> SEQ ID NO 67
<211> LENGTH: 16
<212> TYPE: DNA
<213> ORGANISM: Artificial Sequence
<220> FEATURE:
<223> OTHER INFORMATION: ENHANCER

<400> SEQUENCE: 67
acgtaagcgc ttacga                                                          16

<210> SEQ ID NO 68
<211> LENGTH: 16
<212> TYPE: DNA
<213> ORGANISM: Artificial Sequence
<220> FEATURE:
<223> OTHER INFORMATION: ENHANCER

<400> SEQUENCE: 68
acgtaagcgc ttacgg                                                          16
```

EXPRESSION MODULATING ELEMENTS AND USE THEREOF

FIELD

This disclosure relates to a plant regulatory elements and fragments thereof and their use in altering expression of nucleotide sequences in plants.

REFERENCE TO SEQUENCE LISTING SUBMITTED ELECTRONICALLY

The official copy of the sequence listing is submitted electronically via EFS-Web as an ASCII formatted sequence listing with a file named "7243PCT_ST25.txt" created on Mar. 27, 2018 and having a size of 11 kilobytes and is filed concurrently with the specification. The sequence listing contained in this ASCII formatted document is part of the specification and is herein incorporated by reference in its entirety.

BACKGROUND

Recent advances in plant genetic engineering have opened new doors to engineer plants to have improved characteristics or traits, such as plant disease resistance, insect resistance, herbicidal resistance, and yield improvement. Appropriate regulatory signals present in proper configurations help obtain the desired expression of a gene of interest. These regulatory signals generally include a promoter region, a 5' non-translated leader sequence, an intron, and a 3' transcription termination/polyadenylation sequence.

Expression modulating elements that increase or decrease expression of operably linked nucleotide sequences in plants are desired to modulate the expression of one or more genes of interest.

SUMMARY

A method of modulating expression of an endogenous polynucleotide in a plant cell, the method includes altering one or more nucleotides in a regulatory region of the endogenous polynucleotide such that the regulatory region of the polynucleotide includes an expression modulating element (EME) having at least one copy of a polynucleotide sequence selected from the group consisting of SEQ ID NOS: 1-68, wherein the expression modulating element is heterologous to the endogenous polynucleotide. In an embodiment, the alteration of one or more nucleotides is by genome modification.

In an embodiment, the EME is present within about 10 to about 5000 bp from a transcriptional start site of the endogenous polynucleotide. In an embodiment, the EME further comprises additional copies of the expression modulating element such that about 2× to 10× copies of the EMEs are present in the regulatory region of the endogenous polynucleotide or a recombinant polynucleotide. In an embodiment, when more than one copy of the EME is present, it can be present in one or more of the configurations selected from the group consisting of: head to head, head to tail, tail to head, tail to tail, and a combination thereof. In an embodiment, the additional copies are separated by a spacer sequence, which may include about 1 to 50 nucleotides. In an embodiment, the EME is a combination of one or more copies of heterologous expression elements.

In an embodiment, the expression modulating element is plant-derived; alters the magnitude of expression of the polynucleotide in a tissue preferred manner. In an embodiment, the EME is created in the genome of plant cells by altering no more than 2, 3, 4, 5, 6, 7, 8, 9, 10, 11, 12, 13, 14 or 15 nucleotides in the regulatory region of the endogenous polynucleotide. In an embodiment, when one or more copies of the EMEs are present, the regulatory region is created by altering no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 27, 38, 39 or 40 nucleotides in the regulatory region of the endogenous polynucleotide.

In an embodiment, the EME is located upstream or downstream of the transcriptional start site of the endogenous polynucleotide. In an embodiment, the EME is inserted into the regulatory region of the endogenous polynucleotide such that the expression modulating element is operably linked to the endogenous polynucleotide. In an embodiment, the expression of the endogenous polynucleotide is increased in a plant cell compared to a control plant cell not comprising the EME operably linked to the endogenous polynucleotide.

In an embodiment, for methods utilizing EMEs and compositions containing EMEs, suitable plant cell includes plant cells from monocots and dicots such as, for example, maize, rice, soybean, sunflower, wheat, canola, cotton, or sorghum. In an embodiment, the endogenous polynucleotide is involved in drought tolerance, disease resistance, herbicide tolerance, pest resistance, yield increase, yield stability, nitrogen utilization efficiency or a combination thereof. In an embodiment, the endogenous polynucleotide is a microRNA or a microRNA precursor.

In an embodiment, for methods utilizing EMEs and compositions containing EMEs where genome modification is involved, appropriate techniques include: a site-specific double strand break (DSB) mediated by a polynucleotide-guided endonuclease, zinc finger nuclease, a transcription activator-like effector nuclease (TALEN), polynucleotide-guided recombinase or engineered site-specific meganucleases, or Argonaute or a site-specific base edit mediated by an C•G to T•A or an A•T to G•C base editing deaminase enzymes.

In an embodiment, the EME is operably linked to a heterologous minimal core promoter; a heterologous intron; a heterologous terminator; a heterologous promoter; a heterologous enhancer; a heterologous coding sequence; and a heterologous micro RNA sequence.

A method of increasing expression of a polynucleotide encoding a polypeptide in a plant, the method comprising expressing the polynucleotide by operably linking the polynucleotide with an expression modulating element having at least one copy of the element selected from the group consisting of SEQ ID NOS: 1-68, wherein the expression modulating element is heterologous to the polynucleotide and the expression modulating element is heterologous to a promoter functional in the plant.

In an embodiment, the polypeptide operably linked to one or more EMEs confers herbicide tolerance, insect resistance, disease resistance, abiotic stress tolerance, yield stability, yield increase and a combination thereof. In an embodiment, the EME increases or decreases the expression of a polynucleotide involved in plant architecture or maturity.

In an embodiment, a recombinant DNA construct comprising a polynucleotide sequence comprising any of the sequences set forth in SEQ ID NOS: 1-68, operably linked to at least one heterologous nucleic acid sequence.

In an embodiment, a plant cell comprising an EME selected from the group consisting of SEQ ID NOS: 1-68, wherein the expression modulating element is operably linked to a heterologous polynucleotide, the heterologous polynucleotide encoding a polypeptide. A cell comprising the recombinant DNA construct that includes one or more EMEs described herein; in an embodiment the cell is a plant cell; a bacterial cell such as *Agrobacterium*. In an embodiment, a plant having stably incorporated into its genome such a recombinant construct. In an embodiment, a seed that includes such recombinant DNA construct.

In an embodiment, recombinant DNA construct that contains one or more EMEs described herein is operably linked to at least one heterologous nucleic acid sequence that includes a genetic sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants. In an embodiment, the at least one heterologous sequence comprises a sequence that is substantially similar to an endogenous regulatory sequence of a maize gene.

A method of expressing a coding sequence or RNA in a plant includes expressing the recombinant DNA construct having one or more EMEs, wherein the at least one heterologous sequence comprises a coding sequence or encodes a functional RNA. A method of modulating the expression of a nucleotide sequence of interest in a plant, the method includes expressing a heterologous sequence that is operably linked to an expression modulating element sequence selected from the group consisting of SEQ ID NOS: 1-68. In an embodiment, the heterologous sequence confers an agronomic characteristic selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, nutrient utilization efficiency, nitrogen use efficiency, and salt resistance.

A method of modulating the expression of a nucleotide sequence of interest in a plant, the method includes expressing a polynucleotide sequence that is operably linked to a heterologous expression modulating element that is at least 95% identical to a sequence selected from the group consisting of SEQ ID NOS: 1-68 in combination with an intron or a 5'UTR functional in a plant cell.

A plant stably transformed with a recombinant DNA construct comprising an EME selected from the group consisting of SEQ ID NOS: 1-68 or a sequence that is at least 95% identical to one of SEQ ID NOS: 1-68, wherein the plant comprises the EME operably linked to a heterologous nucleic acid in the genome of the plant, wherein the EME modulates the expression of the heterologous nucleic acid.

A method of modifying the expression of an endogenous gene of a plant, the method comprising introducing an EME selected from the group consisting of SEQ ID NOS: 1-68 or a sequence that is at least 95% identical to one of SEQ ID NOS: 1-68 such that the introduced EME is operably linked to modify the expression of the endogenous gene. In an embodiment, the genome editing is performed through guided Cas9 endonuclease.

An isolated polynucleotide that includes a plant expression modulating element selected from the group consisting of SEQ ID NOS: 1-68 and a combination thereof, wherein the expression modulating element is operably linked to a heterologous promoter sequence. In an embodiment, the polynucleotide having the expression modulating element is operably linked to a heterologous coding sequence. In an embodiment, the heterologous promoter sequence is present in the endogenous genomic sequence. In an embodiment, the EME is present in multiple copies.

A method of generating a population of activation tagged plants comprising one or more copies of expression modulating element, the method comprising transforming a plurality of plants with a recombinant expression cassette comprising the one or more copies of the expression modulating element as an activation tag, wherein the expression modulating element is selected from the group consisting of SEQ ID NOS: 1-68; and generating the population of plants that comprise the activation tag.

A method of identifying one or more plant expression modulating elements (pEME) present in a plant genome, the method comprising (a) performing sequence alignment of a plurality of regulatory sequences with one or more reference expression modulating element (rEME) sequences selected from the group consisting of SEQ ID NOS: 1-68; (b) identifying one or more regions of the regulatory sequences that exhibit sequence identity with zero to about five mismatches to one of the rEME sequences; and (c) expressing a heterologous polynucleotide in an isolated plant cell operably linked to one or more copies of the identified pEME.

A method of high-throughput identification of expression modulating elements derived from plants, the method comprising:
  a) generating recombinant DNA constructs that contain a plurality of genomic fragments enriched for regulatory sequences not containing core promoter sequences with transcriptional start sites, wherein the genomic fragments are operably linked to a heterologous polynucleotide encoding a reporter polypeptide;
  b) expressing the recombinant DNA construct in an isolated plant cell; and
  c) identifying the one or more genomic fragments as expression modulating elements based on the expression levels in the isolated plant cell.

A method of identifying plant-derived expression modulating element, the method comprising (a) determining a minimal region of a previously identified non-plant enhancer element that modulates gene expression in a plant cell; (b) performing sequence search and alignment of a plant genome with the minimal non-plant enhancer element sequence; (c) determining sequence identity matches of the minimal non-plant enhancer element sequences to the regulatory regions of the plant genome, thereby identifying the plant-derived expression modulating element; and (d) synthesizing the plant-derived expression modulating element and performing gene expression analysis with the plant-derived expression modulating element that is operably linked to a heterologous polynucleotide, in a plant cell.

A method of increasing expression of an endogenous polynucleotide sequence, the method comprising introducing a plurality of mutations comprising less than about 10 nucleotide changes at a regulatory region of the endogenous polynucleotide sequence, wherein the plurality of mutations (i) are plant derived; (ii) do not represent a contiguous sequence of more than 7 nucleotides; (iii) do not recreate a complete viral or a bacterial enhancer element, of at least 16 contiguous nucleotides; and (iv) are positioned at an operable distance from a transcriptional start site of the endogenous polynucleotide sequence.

In another embodiment, this disclosure concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In another embodiment, this disclosure concerns a recombinant DNA construct comprising a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

A method of identifying an expression modulating element in a plant genome, the method comprising:

a) identifying a putative expression modulating motif in a regulatory region that is about 20 to about 100 bp upstream of a TATA box or a transcriptional start site, wherein the putative expression modulating motif is about 10 to about 30 contiguous polynucleotides in length;

b) evaluating the expression modulating effects of the putative expression modulating motif in a plant cell; and c) identifying the putative expression modulating motif as the expression modulating element based if the expression modulating motif increases or decreases the expression of a heterologous polynucleotide operably linked to a promoter in the plant cell compared to a control not comprising the expression modulating element.

In another embodiment, the expression modulating element increases expression by at least 3 fold as a single copy compared to the control. In another embodiment, the expression modulating motif is less than 21 bp. In another embodiment, the expression modulating motif is present within about 50 bp upstream of the transcriptional start site.

For the methods and compositions that include the EMEs described herein, suitable fold of expression level compared to an appropriate control without the EMEs, include for example about 1.3, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 75, 80, 90, 100 or more fold, as measured in isolated cell assay, such as for example, in a protoplast assay or as measured in transient expression system or in a plant level, through recombinant or genome editing techniques.

A method of modulating expression of an endogenous polynucleotide in a plant cell, the method includes providing a deaminase polypeptide operably associated with a site-specific DNA binding polypeptide, whereby the deaminase polypeptide engineers one or more base changes such that at least one copy of a polynucleotide comprising the sequence selected from the group consisting of SEQ ID NOS: 1-68 is created in a regulatory region of the endogenous polynucleotide, thereby modulating expression of the endogenous polynucleotide in the plant cell. In an embodiment, the deaminase is an adenine deaminase or a guanine deaminase. In an embodiment, the site-specific DNA binding polypeptide is an inactivated Cas endonuclease (e.g., dCas9). In an embodiment, the inactivated Cas endonuclease is Cas9 or Cpf1, wherein the Cas9 or Cpf1 does not create a double-strand break but provides site-specific binding. In an embodiment, the deaminase is fused to the Cas endonuclease. In an embodiment, the regulatory region is the promoter region of the endogenous polynucleotide. In an embodiment, the endogenous polynucleotide encodes a polypeptide or an RNA (e.g., microRNA (miRNA)) involved in pest protection, disease resistance, herbicide tolerance, drought tolerance, cold tolerance, increased oil and/or protein content, or an improved agronomic characteristic.

BRIEF DESCRIPTION OF THE DRAWINGS AND SEQUENCE LISTING

The disclosure can be more fully understood from the following detailed description and the accompanying drawings and Sequence Listing that form a part of this application, which are incorporated herein by reference.

FIG. 1 is a schematic illustration of an expression cassette showing the possible locations where EME1 was inserted to determine location effect. Locations marked 1-7 correspond to positions referenced in Table 7.

Figure 2:
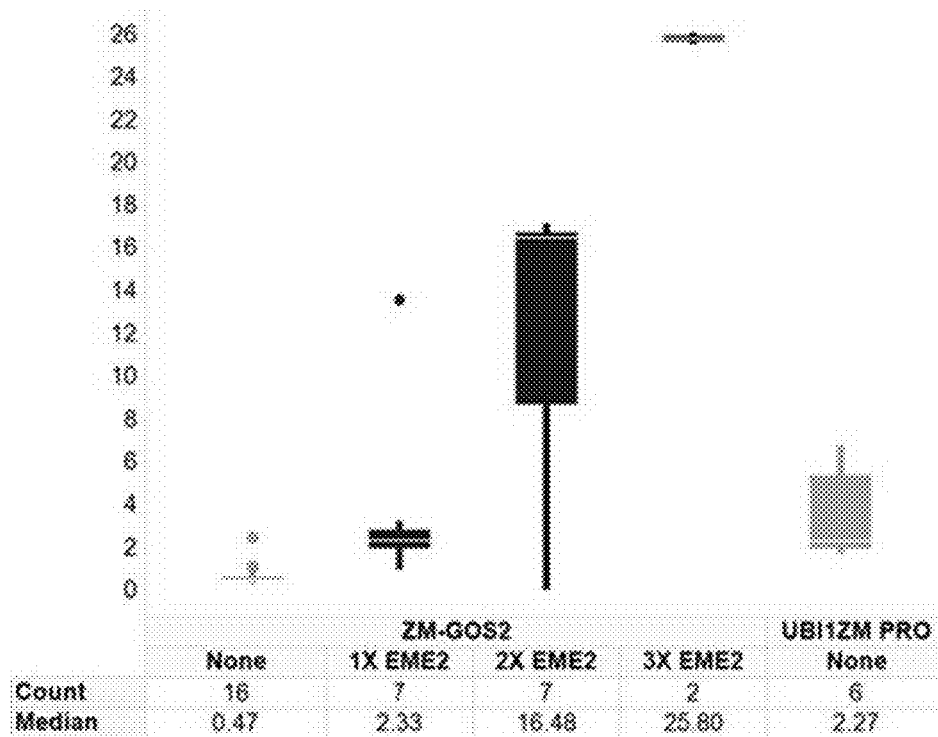

FIG. 2 shows gene expression data from plants containing single copy of the T-DNA with the expression cassette to evaluate EME2 effect on gene expression as measured using qRTPCR on leaf tissue. Count refers to the number of plants assayed. Result from UBI1ZM PRO:UBIZM Intron:ZsGreen:SB-GKAF Term expression cassette is shown as a reference. One copy of EME2 was inserted at −20 of TATA in ZmGOS2 promoter as described in Example 8.

Figure 3:
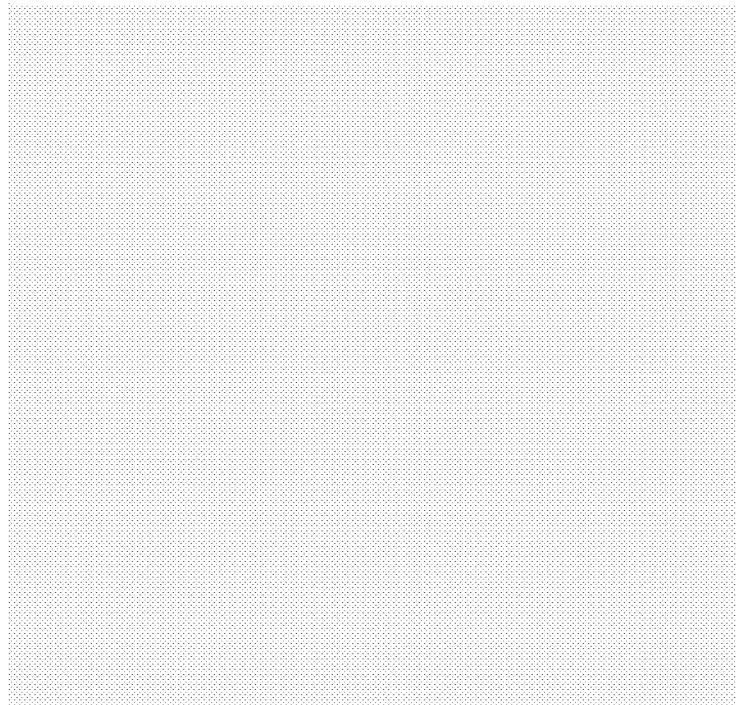
Figure 3:
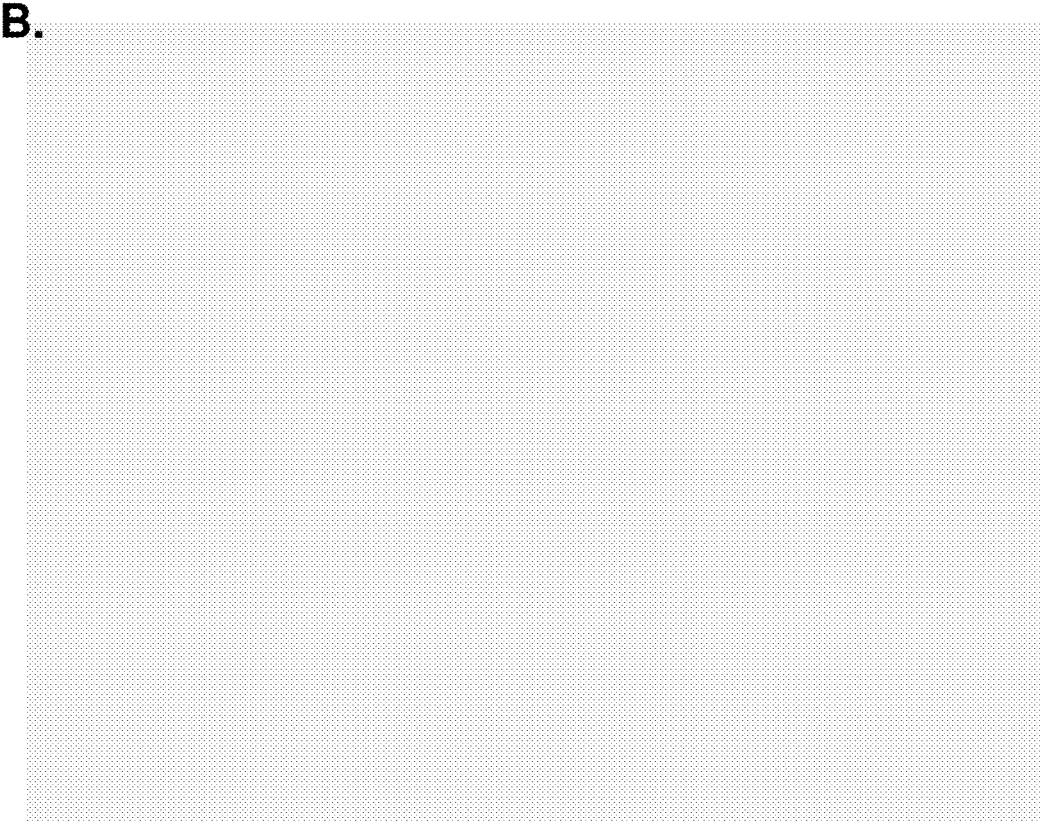

FIG. 3 shows gene expression data from plants containing single copy of the T-DNA with the expression cassette to evaluate EME1 effect on gene expression as measured using qRTPCR on leaf tissue. (A) and (B) show data from separate transformation with the T-DNA being randomly inserted in maize genome. Count refers to the number of plants assayed. Result from UBI1ZM PRO:UBIZM Intron:ZsGreen:SB-GKAF Term expression cassette is shown as a reference. 1-4 copies of EME1 were inserted at −20 of TATA in ZmGOS2 promoter as described in Example 8.

Figure 4:
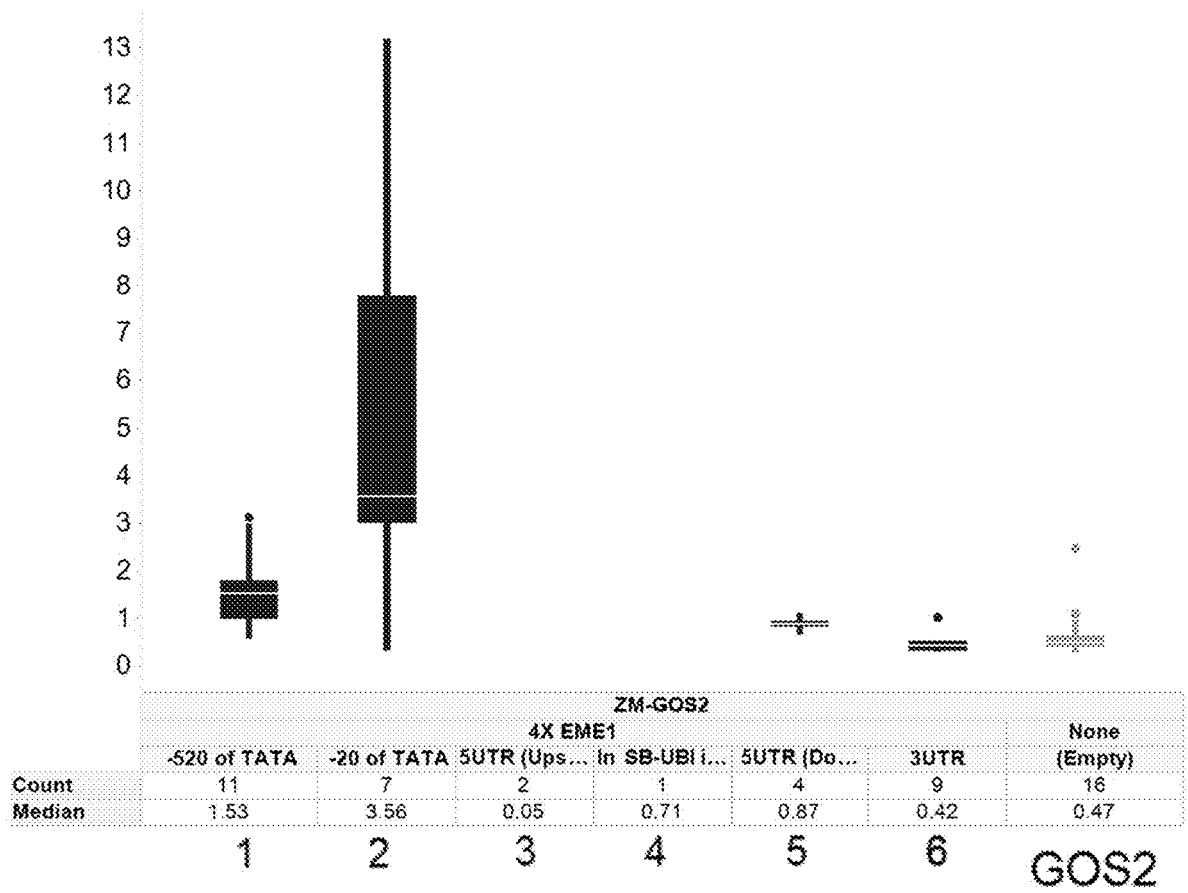

FIG. 4 shows the effect of EME1 location within expression cassette on gene expression as measured using qRTPCR from leaf. Plants containing single copy of the T-DNA with the expression cassette are shown. Count refers to the number of plants assayed. Result from UBI1ZM PRO:UBIZM Intron:ZsGreen:SB-GKAF Term is shown as a reference. Number listed below box plot indicates the location of the 4×EME1 insertion in expression cassette as shown in FIG. 1.

Figure 5:
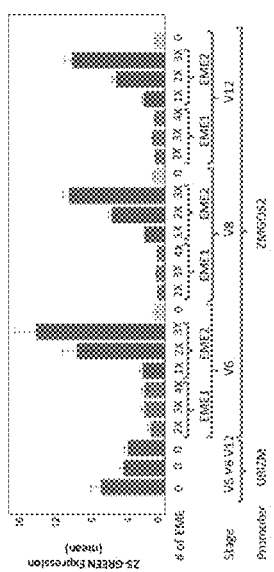

FIG. 5 shows the effect of 2 to 4 copies of EME1 or 1 to 3 copies of EME2 inserted in the maize GOS2 promoter as described in Example 8 on gene expression in T1 leaf tissue at 3 different developmental stages: V6, V8 and V12. The ZmGOS2 promoter with no EME (listed as 0 for # of EME) was used as control to determine expression changes. Gene expression was determined by qRTPCR and is stated in terms of reporter gene expression relative to reference gene. Result from UBI1ZM PRO:UBIZM Intron:ZsGreen:SB-GKAF Term is shown as a control reference.

Figure 6:
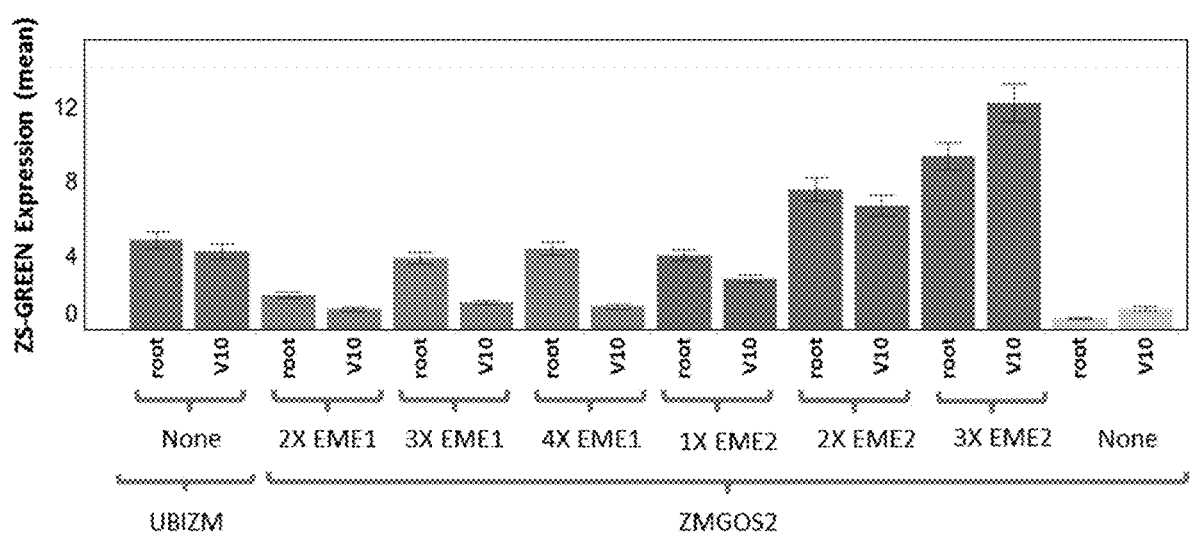

FIG. 6 shows gene expression data from leaf (labeled as V10) or root tissue from T1 single copy plants containing 2 to 4 copies of EME1 or 1 to 3 copies of EME2 inserted in the maize GOS2 promoter as described in Example 8. The ZmGOS2 promoter with no EME (listed as 0 for # of EME) was used as control to determine expression changes. Gene expression was determined by qRTPCR and is stated in terms of reporter gene expression relative to reference gene.

Result from UBI1ZM PRO:UBIZM Intron:ZsGreen:SB-GKAF Term is shown as a control reference.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

TABLE 1

Sequence Listing Description

| SEQ ID NO: | Size (bp) | SEQUENCE 5'-3' |
|---|---|---|
| 1 | 17 | TGACGTAAGGTATGACG |
| 2 | 14 | CGTAAGGTATGACG |
| 3 | 22 | AACAACGTAAGCGCTTACGCAC |
| 4 | 16 | ACGTAAGCGCTTACGC |
| 5 | 14 | CGTAAGCGCTTACG |
| 6 | 14 | CGTAAACAAATACG |
| 7 | 14 | CGTAAACGCTTACG |
| 8 | 17 | TGACGTATGGTATGACG |
| 9 | 14 | CGTAAGGTCTTACG |
| 10 | 14 | CGTAAGTCCTTACG |
| 11 | 14 | CGTAAGTGCTTACG |
| 12 | 14 | CGTAAGGCCTTACG |
| 13 | 14 | CGTAAGACCTTACG |
| 14 | 14 | CGTAAGGACTTACG |
| 15 | 14 | CGTAAGCACTTACG |
| 16 | 14 | CGTAAGGGCTTACG |
| 17 | 14 | CGTAAGCCCTTACG |
| 18 | 14 | CGTAAGTACTTACG |
| 19 | 14 | CGTAAGATCTTACG |
| 20 | 16 | GCGTAAGCGCTTACGC |
| 21 | 16 | AAGTAAGCGCTTACTT |
| 22 | 16 | ACTTAAGCGCTTAAGT |
| 23 | 16 | ACGGAAGCGCTTCCGT |
| 24 | 16 | ACGTGAGCGCTCACGT |
| 25 | 16 | ACGTAGGCGCCTACGT |
| 26 | 16 | ACGTAATCGATTACGT |
| 27 | 16 | GATCGGTATACCGATC |
| 28 | 8 | GCTTACGT |
| 29 | 8 | ACGTAAGC |
| 30 | 16 | ACGTAAGCGCTTACGT |
| 31 | 20 | ACAACGTAAGCGCTTACGCA |

TABLE 1-continued

Sequence Listing Description

| SEQ ID NO: | Size (bp) | SEQUENCE 5'-3' |
|---|---|---|
| 32 | 18 | CAACGTAAGCGCTTACGC |
| 33 | 15 | ACGTAAGCGCTTACG |
| 34 | 15 | CGTAAGCGCTTACGC |
| 35 | 13 | CGTAAGCGCTTAC |
| 36 | 13 | GTAAGCGCTTACG |
| 37 | 10 | TAAGCGCTTA |
| 38 | 8 | AAGCGCTT |
| 39 | 21 | CTGACGTAAGGGATGACGCAC |
| 40 | 16 | GACGTAAGGTATGACG |
| 41 | 15 | ACGTAAGGTATGACG |
| 42 | 13 | GTAAGGTATGACG |
| 43 | 12 | TAAGGTATGACG |
| 44 | 21 | CTGACGTAAGCGCTTACGTAC |
| 45 | 21 | CTGACGTAAGCGCTGACGTAC |
| 46 | 21 | CTGACGTAAGCGCTGACGCAC |
| 47 | 16 | ACGTAAGCGATTACGT |
| 48 | 21 | CTGACGTAAGCGATTACGCAC |
| 49 | 21 | CTGACGTAAGCGATTACGTAC |
| 50 | 21 | CTGACGTAAGGGATTACGTAC |
| 51 | 22 | AATGACGTAAGCGCTTACGCAC |
| 52 | 22 | AATGACGTAAGCGCTGACGCAC |
| 53 | 12 | CGTAAGGTATGA |
| 54 | 12 | GTAAGGTATGAC |
| 55 | 12 | GACGTAAGGTAT |
| 56 | 13 | ACGTAAGGTATGA |
| 57 | 13 | CGTAAGGTATGAC |
| 58 | 13 | GACGTAAGGTATG |
| 59 | 14 | ACGTAAGGTATGAC |
| 60 | 14 | GACGTAAGGTATGA |
| 61 | 15 | GACGTAAGGTATGAC |
| 62 | 11 | TAAGCGCTTAC |
| 63 | 12 | GTAAGCGCTTAC |
| 64 | 12 | TAAGCGCTTACG |
| 65 | 14 | GTAAGCGCTTACGC |
| 66 | 16 | AACGTAAGCGCTTACG |

TABLE 1-continued

Sequence Listing Description

| SEQ ID NO: | Size (bp) | SEQUENCE 5'-3' |
|---|---|---|
| 67 | 16 | ACGTAAGCGCTTACGA |
| 68 | 16 | ACGTAAGCGCTTACGG |
| 69 | | |

DETAILED DESCRIPTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

An "isolated polynucleotide" generally refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Expression modulating/modulation element" or "EME" as used herein refers to a nucleotide sequence that up or down-regulates the expression of one or more plant genes. EME may have one or more copies of the same sequence arranged head-to-head, tail-to-head, or head-to-tail or a combination thereof configurations. EMEs are derived from plant sequences, or from bacterial or viral enhancer elements.

A regulatory element generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

An enhancer element is any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) is defined as any nucleic acid molecule which inhibits the transcription when functionally linked to a promoter regardless of relative position.

"Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

"Promoter functional in a plant" is a promoter capable of initiating transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" generally refers to a promoter whose activity is determined by developmental events.

"Constitutive promoter" generally refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

A "heterologous nucleotide sequence" generally refers to a sequence that is not naturally occurring with the EME of the disclosure. While this nucleotide sequence is heterologous to the EME sequence, it may be homologous, or native, or heterologous, or foreign, to the plant host. However, it is recognized that the instant EMEs may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

A "functional fragment" refers to a portion or subsequence of the sequence described in the present disclosure in which, the ability to modulate gene expression is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the EMEs of the present disclosure is any nucleic acid fragment that is capable of modulating the expression of a coding sequence or functional RNA in a similar manner to the EMEs of the present disclosure.

The polynucleotide sequence of the EMEs of the present disclosure (e.g., SEQ ID NOS: 1-68), may be modified or altered to enhance their modulation characteristics. As one of ordinary skill in the art will appreciate, modification or alteration can also be made without substantially affecting the gene expression function. The methods are well known to those of skill in the art. Sequences can be modified, for example by insertion, deletion, or replacement of template sequences through any modification approach.

A "variant promoter" as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant EMEs of the present disclosure include, but are not limited to, combining EME elements of different EMEs or duplicating portions or regions of one or more EMEs. Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present disclosure, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides. In another aspect of the present disclosure, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1200, 1300, 1400, 1500, 2000 contiguous nucleotides and further may include an EME comprising one of SEQ ID NOS: 1-68. Further, these regulatory fragments include one of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 or a combination thereof. The nucleotides of such fragments generally comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

The transitional phrase "consisting essentially of" generally refers to a composition, method that includes materials, steps, features, components, or elements, in addition to those literally disclosed, provided that these additional materials, steps, features, components, or elements do not materially affect the basic and novel characteristic(s) of the claimed subject matter, e.g., one or more of the claimed expression modulating elements (EMEs).

The isolated promoter sequence comprised in the recombinant DNA construct of the present disclosure can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts. Similarly, a "moderate constitutive" promoter is somewhat weaker than a strong constitutive promoter like the maize ubiquitin promoter.

In addition to modulating gene expression, the expression modulating elements disclosed herein are also useful as probes or primers in nucleic acid hybridization experiments. The nucleic acid probes and primers of the EMEs hybridize under stringent conditions to a target DNA sequence. A "probe" is generally referred to an isolated/synthesized nucleic acid to which, is attached a conventional detectable label or reporter molecule, such as for example, a radioactive isotope, ligand, chemiluminescent agent, bioluminescent molecule, fluorescent label or dye, or enzyme. Such detectable labels may be covalently linked or otherwise physically associated with the probe. "Primers" generally referred to isolated/synthesized nucleic acids that hybridize to a complementary target DNA strand which is then extended along the target DNA strand by a polymerase, e.g., a DNA polymerase. Primer pairs often used for amplification of a target nucleic acid sequence, e.g., by the polymerase chain reaction (PCR) or other conventional nucleic-acid amplification methods. Primers are also used for a variety of sequencing reactions, sequence captures, and other sequence-based amplification methodologies. Primers are generally about 15, 20, 25 nucleotides or more, and probes can also be longer about 30, 40, 50 and up to a few hundred base pairs. Such probes and primers are used in hybridization reactions to target DNA or RNA sequences under high stringency hybridization conditions or under lower stringency conditions, depending on the need.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2× SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this disclosure are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 71% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, the isolated EME sequence comprised in the recombinant DNA construct of the present disclosure comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOS: 1-68. It is known to one of skilled in the art that a 5' UTR region can be altered (deletion or substitutions of bases) or replaced by an alternative 5'UTR while maintaining promoter activity.

A "substantially similar sequence" generally refers to variants of the disclosed sequences such as those that result from site-directed mutagenesis, as well as synthetically derived sequences. A substantially similar sequence of the present disclosure also generally refers to those fragments of a particular promoter nucleotide sequence disclosed herein that operate to promote the constitutive expression of an operably linked heterologous nucleic acid fragment. These promoter fragments comprise at least about 20 contiguous nucleotides, at least about 50 contiguous nucleotides, at least about 75 contiguous nucleotides, preferably at least about 100 contiguous nucleotides of the particular promoter nucleotide sequence disclosed herein or a sequence that is at least 95 to about 99% identical to such contiguous sequences. The nucleotides of such fragments will usually include the TATA recognition sequence (or CAAT box or a CCAAT) of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. Variants of these promoter fragments, such as those resulting from site-directed mutagenesis, are encompassed by the compositions of the present disclosure.

"Codon degeneracy" generally refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect similar or identical sequences including, but not limited to, the Megalign® program of the LASERGENE® bioinformatics computing suite (DNASTAR® Inc., Madison, WI). Unless stated otherwise, multiple alignment of the sequences provided herein were performed using the Clustal V method of alignment (Higgins and Sharp (1989) CAB/OS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CAB/OS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid). A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN generally refers to a BLAST program that compares a nucleotide query sequence against a nucleotide sequence database.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" generally refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

"Chimeric gene" or "recombinant expression construct", which are used interchangeably, includes any gene that is not a native gene, comprising regulatory and coding sequences that are not found together in nature. Accordingly, a chimeric gene may comprise regulatory sequences and coding sequences that are derived from different sources.

"Coding sequence" generally refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" generally refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") generally refers to RNA that is without introns and that can be translated into protein by the cell. "cDNA" generally refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA generally refers to RNA transcript that includes mRNA and so can be translated into protein within a cell or in vitro. "Antisense RNA" generally refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" generally refers to antisense RNA, ribozyme RNA, or other RNA that may not be translated but yet has an effect on cellular processes.

The term "operably linked" or "functionally linked" generally refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, generally refers to the production of a functional end-product e.g., an mRNA or a protein (precursor or mature).

The term "expression cassette" as used herein, generally refers to a discrete nucleic acid fragment into which a nucleic acid sequence or fragment can be cloned or synthesized through molecular biology techniques.

Expression or overexpression of a gene involves transcription of the gene and translation of the mRNA into a precursor or mature protein. "Antisense inhibition" generally refers to the production of antisense RNA transcripts capable of suppressing the expression of the target protein. "Overexpression" generally refers to the production of a gene product in transgenic organisms that exceeds levels of production in normal or non-transformed organisms. "Co-suppression" generally refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

As stated herein, "suppression" includes a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" generally refers to an enzyme that is produced naturally in a non-transgenic or wild type cell. The terms "non-transgenic" and "wild type" are used interchangeably herein.

"Altering expression" or "modulating expression" generally refers to the production of gene product(s) in plants in amounts or proportions that differ significantly from the amount of the gene product(s) produced by the corresponding wild-type plants (i.e., expression is increased or decreased).

"Transformation" as used herein generally refers to both stable transformation and transient transformation.

"Stable transformation" generally refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" generally refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Genome" as it applies to plant cells encompasses not only chromosomal DNA found within the nucleus, but organelle DNA found within subcellular components (e.g., mitochondrial, plastid) of the cell.

"Genetic modification" generally refers to modification of any nucleic acid sequence or genetic element by insertion, deletion, or substitution of one or more nucleotides in an endogenous nucleotide sequence by genome editing or by insertion of a recombinant nucleic acid, e.g., as part of a vector or construct in any region of the plant genomic DNA by routine transformation techniques. Examples of modification of genetic components include, but are not limited to, promoter regions, 5' untranslated leaders, introns, genes, 3' untranslated regions, and other regulatory sequences or sequences that affect transcription or translation of one or more nucleic acid sequences.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

"Progeny" comprises any subsequent generation of a plant.

The heterologous polynucleotide can be stably integrated within the genome such that the polynucleotide is passed on to successive generations. The heterologous polynucleotide may be integrated into the genome alone or as part of a recombinant DNA construct. The alterations of the genome (chromosomal or extra-chromosomal) by conventional plant breeding methods, by genome editing procedures that do not result in an insertion of a foreign polynucleotide, or by naturally occurring events such as random cross-fertilization, non-recombinant viral infection, non-recombinant bacterial transformation, non-recombinant transposition, or spontaneous mutation are also methods of modifying a host genome.

"Transient expression" generally refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, New York, 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, CT). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and generally refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation may change accordingly. General categories of genes of interest include, but are not limited to, those genes involved in information, such as zinc fingers, those involved in communication, such as kinases, and those involved in housekeeping, such as heat shock proteins. More specific categories, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, Northern Corn Leaf Blight, head smut, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

In certain embodiments, the present disclosure contemplates the transformation of a recipient cell with more than one advantageous gene. Two or more genes can be supplied in a single transformation event using either distinct gene-encoding vectors, or a single vector incorporating two or more gene coding sequences. Any two or more genes of any description, such as those conferring herbicide, insect, disease (viral, bacterial, fungal, and nematode), or drought resistance, oil quantity and quality, or those increasing yield or nutritional quality may be employed as desired.

This disclosure concerns a recombinant DNA construct comprising an isolated nucleic acid fragment comprising a constitutive EMEs. This disclosure also concerns a recombinant DNA construct comprising a promoter wherein said promoter consists essentially of the nucleotide sequence set forth in SEQ ID NO:1 or 2, or an isolated polynucleotide comprising a promoter wherein said promoter comprises the nucleotide sequence set forth in SEQ ID NOS: 1-2 and 5-6 or a functional fragment of SEQ ID NOS: 1-2 and 5-6.

It is clear from the disclosure set forth herein that one of ordinary skill in the art could perform the following procedure:

1) operably linking the nucleic acid fragments containing the EMEs, intron or the 5'UTR sequences to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming EMEs, intron or the 5'UTR sequences: reporter gene expression cassettes into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the EMEs, intron or the 5'UTR sequences in various cell types of transgenic plant tissues, e.g., leaves, roots, flowers, seeds, transformed with the chimeric EMEs, intron or the 5'UTR sequences: reporter gene expression cassette by assaying for expression of the reporter gene product.

In another aspect, this disclosure concerns a recombinant DNA construct comprising at least one heterologous nucleic acid fragment operably linked to any promoter, or combination of promoter elements, of the present disclosure. Recombinant DNA constructs can be constructed by operably linking the nucleic acid fragment of the disclosure EMEs or a fragment that is substantially similar and functionally equivalent to any portion of the nucleotide sequence set forth in SEQ ID NOS: 1-56 to a heterologous nucleic acid fragment. Any heterologous nucleic acid fragment can be used to practice the disclosure. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present disclosure.

In another aspect, this disclosure concerns a recombinant DNA construct comprising at least one gene that provides drought tolerance operably linked to EMEs or a fragment, or combination of promoter elements, of the present disclosure. In another aspect, this disclosure concerns a recombinant DNA construct comprising at least one gene that provides insect resistance operably linked to EMEs or a fragment, or combination of promoter elements, of the present disclosure. In another aspect, this disclosure concerns a recombinant DNA construct comprising at least one gene that increases nitrogen use efficiency and/or yield, operably linked to EMEs or a fragment, or combination of promoter elements, of the present disclosure. In another aspect, this disclosure concerns a recombinant DNA construct comprising at least one gene that provides herbicide resistance operably linked to EMEs or a fragment, or combination of promoter elements, of the present disclosure.

In another embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

I. Gene Editing

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 *Nature Methods* Vol. 10: 957-963.)

The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

In addition to the double-strand break inducing agents, site-specific base conversions can also be achieved to engineer one or more nucleotide changes to create one or more EMEs described herein into the genome. These include for example, a site-specific base edit mediated by an C•G to T•A or an A•T to G•C base editing deaminase enzymes (Gaudelli et al., Programmable base editing of A•T to G•C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific positions. It is understood that based on the methods and embodiments described herein utilizing a guided Cas system one can now tailor these methods such that they can utilize any guided endonuclease system.

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The terms "target site", "target sequence", "target site sequence", "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an guidepolynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

The terms "knock-in", "gene knock-in", "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and, Tijssen (1993) Laboratory Techniques in Biochemistry and Molecular Biology—Hybridization with Nucleic Acid Probes, (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

In an embodiment, through genome editing approaches described herein and those available to one of ordinary skill in the art, specific motifs of one or more regulatory elements of the EMEs disclosed herein can be engineered to modulate the expression of one or more host plant endogenous genes.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569, 834, 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); *papaya* (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, CA, 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

Another general application of the EMEs of the disclosure is to construct chimeric polynucleotides that can be used to increase or reduce expression of at least one heterologous nucleic acid fragment in a plant cell. To accomplish this, a chimeric gene designed for gene silencing of a heterologous nucleic acid fragment can be constructed by linking the fragment to the EMEs of the present disclosure. Alternatively, a chimeric gene designed to express antisense RNA for a heterologous nucleic acid fragment can be constructed by linking the fragment in reverse orientation to the EMEs of the present disclosure. Either the cosuppression or antisense chimeric gene can be introduced into plants via transformation. Transformants wherein expression of the heterologous nucleic acid fragment is decreased or eliminated are then selected.

This disclosure also concerns a method of altering (increasing or decreasing) the expression of at least one heterologous nucleic acid fragment in a plant cell which comprises:
  (a) transforming a plant cell with the recombinant expression construct described herein;
  (b) growing fertile mature plants from the transformed plant cell of step (a);
  (c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

In an embodiment, the EME is present within about 10 to about 5000 bp from a transcriptional start site of the endogenous polynucleotide. This location range also includes about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 1000, 2000, 3000, 4000 and 5000 nucleotides from the TSS. In an embodiment, the EME further comprises additional copies of the expression modulating element such that about 2× to 10× copies of the EMEs are present in the regulatory region of the endogenous polynucleotide or a recombinant polynucleotide. Additional number of copies such as 3×, 4×, 5×, 6×, 7×, 8×, 9× are also suitable based on the need to express a particular polynucleotide higher or lower depending upon e.g., a trait of interest. In an embodiment, when more than one copy of the EME is present, it can be present in one or more of the configurations selected from the group consisting of: head to head, head to tail, tail to head, tail to tail, and a combination thereof. In an embodiment, the additional copies are separated by a spacer sequence, which may include about 1 to 50 nucleotides. In an embodiment, the EME is a combination of one or more copies of heterologous expression elements. Suitable length of a spacer that is present between one or more EMEs of the present disclosure include for example, about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100 or more contiguous polynucleotides. The spacer sequences may include intron elements or other non-coding sequences that do not materially alter the function intended to be conveyed by the EMEs.

EXAMPLES

The present disclosure is further defined in the following Examples, in which parts and percentages are by weight and degrees are Celsius, unless otherwise stated. Sequences of promoters, cDNA, adaptors, and primers listed in this disclosure all are in the 5' to 3' orientation unless described otherwise. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Maize Protoplast Assay and Quantification of Reporter Gene

Expression modulating elements (EMEs) were identified and appropriate transformation vectors with a reporter gene (e.g., ZsGreen) were constructed. Those vectors were tested in maize leaf protoplasts. This protoplast expression assay uses a modified version of this commonly used protocol to facilitate the delivery of known plasmid DNA to cells isolated from maize inbred leaf mesophyll cells. The transfection method utilized in this assay is the polyethelene glycol 40% w/v mediated transfection.

The quantification methodology used in the protoplast expression assay is based around the BioTek Cytation5 inverted microscope imager. Images are taken of the transfected protoplast populations using excitation and emission spectra as determined based on the fluorescent markers chosen for the experiment. When quantification of a known element is required, a dual cassette expression vector is used. The normalization cassette consists of a strong constitutive promoter Seteria UBI along with Seteria UBI intron driving TagRFP; this cassette also acts as a transfection control to monitor transfection efficiency. The experimental cassette contains the DNA sequence being evaluated with ZsGreen as the reporter gene. Post imaging processing is carried out primarily in the BioTek Gen5 software. Using a circularity, size, and presence of TagRFP fluorescence algorithm, positively transfected cells were identified and the relative fluorescence based on pixel intensity was recorded. The fluorescence recorded from the GFP channel is normalized to the RFP in order to quantify on a cell by cell basis. The arithmetic mean is calculated for each experimental entity and compared to the appropriate control to determine significance based on a p value <0.5 even though in most cases significance was established at a higher stringency (p value <0.0001). In other cases, the geometric mean is calculated for each experimental entity and ANOVA was done using Tukey with an alpha value of 5%.

Example 2

Multimer Effects of Tested EMEs

Several configurations of the EMEs were tested to determine the multimer effects of for modulating gene expression. Data for EMEs designated as 4×EME1, 3×EME2, 1× EME1, 2×EME1, and 3×EME1 are shown in Table 2 below. EME1 and EME2 are sequences identified from maize genomic sequences.

TABLE 2

EMEs and effect on location

| Activation element | SEQ ID NO for 1X EME | Standard Error | P Value | Fold Change relative to Control | Replicates |
|---|---|---|---|---|---|
| Control - CAMV35S PRO (MIN)- No EME | | 0.01511 | | | 5240 |
| 1X EME1 | 1 | 0.01876 | 0.8432 | 1.07 | 4589 |
| 2X EME1 | 1 | 0.01859 | 0.0067 | 2.02 | 4751 |
| 3X EME1 | 1 | 0.01838 | <.0001 | 5.33 | 4973 |
| 4X EME1 | 1 | 0.01847 | <.0001 | 6.88 | 4871 |
| 1X EME2 | 3 | 0.01865 | <.0001 | 3.10 | 4708 |
| 2X EME2 | 3 | 0.01993 | <.0001 | 39.76 | 3721 |
| 3X EME2 | 3 | 0.01783 | <.0001 | 72.21 | 5691 |

In order to determine if EME1 (SEQ ID NO: 1) affects expression levels in maize protoplast assay, expression cassettes containing 1-4× copies of EME1 (SEQ ID NO: 1) cloned upstream of a minimal Cauliflower Mosaic Virus (CaMV) 35S promoter driving expression of the reporter gene ZsGreen were constructed. In the control construct containing CaMV 35S minimal promoter driving ZsGreen, there is no detectable level of ZsGreen fluorescence. When 1-4 copies of EME1 are cloned upstream of the CaMV 35S minimal promoter, 1-6 fold increase was assessed respectively (Table 2). A significant change in expression was calculated with ZsGreen fluorescence observed in protoplasts containing the expression cassettes with 2-4 copies of EME1 cloned upstream of CaMV 35S minimal promoter.

In addition to EME1, a second maize sequence (EME2, SEQ ID NO: 3) was evaluated in a similar manner with the CaMV 35S minimal promoter. When 1-3 copies of EME2 (SEQ ID NO: 3) or one copy of EME1 with a single copy of EME2 were cloned upstream of the minimal CaMV 35S promoter, a significant difference in expression levels in maize protoplasts was determined with the fold change ranging from about 3-fold to about 72-fold, providing an effective tool kit to modulate gene expression endogenously using plant derived enhancer elements (Table 2). Both EME1 and EME2 increased expression level of the tested regulatory elements to drive expression of a polynucleotide (e.g. ZsGreen) in plant cells (e.g. maize cells).

Example 3

Multimer Effects of Tested EMEs for Modulating Expression of a Moderate Constitutive Promoter Several multimer configurations of the ZM-AS-1 L and Zm-AS2 EME were tested to determine gene expression modulation driven by a moderate constitutive promoter (Zm-GOS2: SB-Ubi intron). Data for the 1×, 2×, 3× and 4× versions of the tested EME sequences for the expression modulation of the ZmGOS2 promoter are shown in Table 3.

TABLE 3

Multimer effects of EMEs on Moderate Constitutive Plant Promoter

| PROMOTER | Activation element | SEQ ID NO for 1X EME | P Value | Fold Change | Replicates |
|---|---|---|---|---|---|
| ZM-GOS2 PRO: SB-UBI INTRON | Control (No EME) | | | | 1886 |
| ZM-GOS2 PRO: SB-UBI INTRON | 1X EME1 | 1 | <.0001 | 2.64 | 3659 |
| ZM-GOS2 PRO: SB-UBI INTRON | 2X EME1 | 1 | <.0001 | 4.01 | 3513 |
| ZM-GOS2 PRO: SB-UBI INTRON | 3X EME1 | 1 | <.0001 | 4.61 | 1004 |
| ZM-GOS2 PRO: SB-UBI INTRON | 4X EME1 | 1 | <.0001 | 4.55 | 2219 |
| ZM-GOS2 PRO: SB-UBI INTRON | 1X EME1/ 1X EME2 | 2/3 | <.0001 | 4.98 | 2329 |
| ZM-GOS2 PRO: SB-UBI INTRON | 1X EME2 | 3 | <.0001 | 3.88 | 2841 |
| ZM-GOS2 PRO: SB-UBI INTRON | 2X EME2 | 3 | <.0001 | 5.37 | 2644 |
| ZM-GOS2 PRO: SB-UBI INTRON | 3X EME2 | 3 | <.0001 | 5.81 | 2952 |

EME1 was also evaluated with a constitutive promoter (e.g. ZmGOS2, see for example, U.S. Pat. No. 6,504,083) to determine how expression levels of ZsGreen changed in this context. One to four copies of EME1 (SEQ ID NO: 1) were cloned in the −50 location of the transcriptional start site (TSS) in the moderate maize constitutive promoter ZmGOS2. When the control vector with no EME sequence was transfected into maize protoplasts, ZsGreen fluorescence was observed and quantified, to establish the baseline. When 1-4 copies of EME1 (SEQ ID NO: 1) were present in the ZmGOS2 promoter, the value quantified increased 2.6-4.6 fold over the value calculated for the control vector (Table 3).

When 1-3 copies of EME2 (SEQ ID NO: 3) was cloned at −50 location upstream of the TSS in the ZmGOS2 promoter, a significant change in expression (3.9-5.8-fold change, Table 3) was measured when compared to the control vector with no EME2 sequence. Thus, both EME1 and EME2 were demonstrated to be expression modulating elements, which increased expression of polynucleotides plant cells when positioned at an operable distance from the transcriptional start size in the plant cells.

Example 4

Expression Modulation Effects of Tested EMEs on Various Plant Promoters

Several configurations of the EMEs were tested to determine the effects gene expression modulation of a variety of plant promoters. Data for the 4×EME1 evaluated for the promoters described below are shown in Table 4.

TABLE 4

EMEs and expression modulation of plant promoters

| PROMOTER TESTED | Activation element | Activation element Location | P Value | Fold Change relative to Control | Replicates |
|---|---|---|---|---|---|
| UBI1ZM PRO: UBI1 INTRON1 | Control | No EME | — | — | 3539 |
| UBI1ZM PRO: UBI1 INTRON1 | 4X EME1 | −50 of TSS | <.0001 | 1.31 | 3218 |
| ZM-ADF4 PRO: ZM-ADF4 INTRON | Control | No EME | — | — | 4080 |
| ZM-ADF4 PRO: ZM-ADF4 INTRON | 4X EME1 | −50 of TSS | <.0001 | 2.99 | 2101 |
| OLE PRO | Control | No EME | — | — | 5375 |
| OLE PRO | 4X EME1 | −50 of TSS | <.0001 | 35.78 | 3131 |
| ZM-GOS2 PRO: SB-UBI INTRON | Control | No EME | — | — | 11748 |
| ZM-GOS2 PRO: SB-UBI INTRON | 4X EME1 | −50 of TSS | <.0001 | 2.55 | 10272 |

EME1 (SEQ ID NO: 1) was also evaluated in maize protoplasts with three additional promoters: a strong constitutive promoter (UBIZM), a weak constitutive promoter (ZmADF4) and a seed-specific promoter (ZmOLE). For each of these promoters 4 copies of EME1 was cloned—50 location upstream of the TSS with ZsGreen as the reporter gene, transfected into maize leaf protoplasts and quantified with the results shown in Table 4. Even though maize UBI promoter along with maize UBI intron driving ZsGreen showed strong fluorescence in maize protoplasts, the addition of the 4 copies of EME1 resulted in a significant increase in expression, compared to the UBI promoter driven reporter gene expression. Overall, the maize ADF4 promoter with the Sorghum UBI intron driving ZsGreen resulted in a lower expression of ZsGreen fluorescence than either maize UBI or maize GOS2 promoters with same intron. Insertion of 4 copies of EME1 in this ZmADF4 promoter expression cassette resulted in a 3-fold increase in ZsGreen fluorescence. When ZmOLE drove expression of ZsGreen in maize leaf protoplasts, no visible ZsGreen fluorescence is observed. However, when 4 copies of EME1 were inserted into this maize OLE promoter, ZsGreen fluorescence was visible in maize leaf protoplasts. This significant change in ZsGreen fluorescence resulted in a 35-fold increase over the control ZmOLE construct. With significant increases in reporter gene expression levels determined independently with 5 different promoters, EME1 was demonstrated to be an expression modulating element capable of significantly modulating gene expression in plant cells. Similarly, EME2 also increased gene expression in multiple promoter configurations demonstrating that EME2 is also useful in modulating gene expression, e.g., FIGS. 5-6.

Example 5

Effects of Truncated Sequence Variations of Tested EMEs

Several sequence variations of the EME2 were tested to determine sequence wobble effects for modulating gene expression. Data for the EME2 sequence variations evaluated for the expression modulation of the ZmGOS2 promoter are shown in Table 5.

TABLE 5

Truncation Effects of EME2

A. First set of sequence variations

| Activation element | SEQ ID NO for EME | P Value | Fold Change relative to Control | Replicates |
|---|---|---|---|---|
| Control (No EME); ZM- GOS2 PRO: SB-UBI INTRON | | — | — | 4211 |
| OCS ENH | 30 | <.0001 | 2.84 | 3340 |
| OCS ENH | 39 | <.0001 | 3.17 | 3788 |
| EME2 (16 bp) | 4 | <.0001 | 2.65 | 4321 |
| EME2 (14 BP) | 5 | <.0001 | 3.40 | 4926 |
| EME2 (13 BP) | 35 | <.0001 | 0.84 | 4189 |
| EME2 (10 BP) | 37 | 0.9724 | 1.00 | 4035 |
| EME2 (8 BP) | 38 | <.0001 | 0.81 | 5108 |

B. Second set of sequence variations

| SEQ ID | Class | Size | Mean | Significance grouping |
|---|---|---|---|---|
| 30 | OCS ENH | 16 bp | 5.802 | a |
| 33 | EME2 | 15 bp | 5.787 | a |
| 4 | EME2 | 16 bp | 5.613 | a |
| 66 | EME2 | 16 bp | 5.506 | a |
| 34 | EME2 | 15 bp | 4.674 | b |
| 65 | EME2 | 14 bp | 3.622 | c |
| 5 | EME2 | 14 bp | 3.291 | d |
| 36 | EME2 | 13 bp | 2.237 | e |
| | Control | No EME | 1.777 | f |
| 35 | EME2 | 13 bp | 1.305 | g |
| 62 | EME2 | 11 bp | 1.267 | gh |
| 63 | EME2 | 12 bp | 1.224 | h |
| 64 | EME2 | 12 bp | 1.210 | h |

A 16-bp palindromic octopine synthase (ocs) element from *Agrobacterium* sequence (SEQ ID NO: 30) along with another 21 bp ocs enhancer family member sequence (SEQ ID NO:39) were included to evaluate the maize EME2 sequence variations compared to these elements in maize protoplasts. A series of EME2 sequences ranging in size from 16 bp to 8 bp (SEQ ID NO: 4, SEQ ID NO: 5, SEQ ID 35, SEQ ID NO: 37 and SEQ ID NO: 38) was created by sequentially removing a base from each end of the sequence. The 13 bp variation was created by a flanking base in the ZmGOS2 promoter next to the 12 bp variation recreated a 13 bp sequence of the original EME2. Each EME2 variation was inserted at the −50 location of the TSS in the ZmGOS2 promoter in the previously described. The elements ranging in length from 16 bp (SEQ ID NO: 4) to 14 bp (SEQ ID NO: 5) EME2 significantly changed expression (Table 5A) while other sequences 13 bp or less EME2 sequences lead to either no significant change or a significant decrease in quantified expression levels. After these results, a systematic dissection of the regulatory element was done by creating size variations from 16 bp to 11 bp. Variations were created by first removing a base from the 5' end resulting in elements ranging in size from 15 bp to 14 bp; a second series was created by removing a base from the 3' end resulting in the same range of elements as the 5' series. Variations smaller than 14 bp were created by removing nucleotides from each end of EME2. For example, an 11 bp element (SEQ ID NO: 62) was created by removing 3 nucleotides from the 5' end and 2 nucleotides from the 3' end. Each shortened EME2 sequence was inserted at the −50 location of the TSS in the ZmGOS2 promoter described previously in an expression cassette containing the Sorghum intron, a reporter gene (e.g. ZsGreen) and sorghum gamma kafarin (GKAF) terminator, and tested in maize leaf protoplasts. Maize GOS2 promoter sequence flanking the EME variations was reviewed to ensure that neighboring bases did not recreate a longer EME version or a sequence similar to 16 bp ocs enhancer sequence (SEQ ID NO:47). In the case of the 13 bp truncated variations, one EME2 (SEQ ID 36) showed a significant increase in expression while the other 13 bp variation (SEQ ID 35) resulted in significantly lower expression from the control (Table 5B). Based on these experiments, a 13-bp EME2 sequence (SEQ ID NO:36) was a smaller fragment sequence tested to be sufficient to modulate fluorescence in maize.

The truncated 14 bp EME2 (SEQ ID NO: 5) inserted in −50 of the TSS in the ZmGOS2 promoter significantly increased gene expression in plant cells than the other tested sequences in Table 5A. The flanking sequence of this variation had a "T" as the flanking sequence creating ACGT at the 3' end of this EME2 element. Thus, a series of constructs were created similar as described above in which the immediately flanking sequence of the 15 bp EME2 (SEQ ID NO: 33) located 50 bp upstream of the TSS of the ZmGOS2 promoter was changed to "A" or "G". These two variations were compared to the "T", which recreates the ocs enhancer (SEQ ID NO: 30) and the original EME2 16 bp sequence (SEQ ID NO: 4) in which "C" is located at this position. ANOVA shows that there is a significant difference in expression for each comparison (Table 6). The ocs enhancer resulted in a greater increase in reporter gene expression followed by the original 16 bp EME2 and the EME with "A" in the last base location while a "G" in the last base results in the lowest expression level. These results demonstrate that expression levels can be modulated by altering the last base of a 16 bp EME2 sequence.

TABLE 6

Effects on gene expression by modification of last base of EME2

| SEQ ID | Class | Last Base | Mean | Significance grouping |
|---|---|---|---|---|
| 30 | OCS ENH | T | 6.836 | a |
| 4 | EME2 | C | 5.987 | b |
| 67 | EME2 | A | 5.146 | c |
| 68 | EME2 | G | 3.569 | d |

A similar approach as described for EME2 was taken to determine a shorter fragment EME1 sequence that affected expression level in maize protoplasts. These EME1 variations were inserted at the −50 location of the TSS in the ZmGOS2 promoter in the previously described expression cassette. AS-1 a 21 bp enhancer sequence (SEQ ID NO: 39), was included to evaluate how well the maize EME1 sequence variations compared to this element in maize protoplasts. ANOVA shows each EME1 variation significantly increased expression when compared to the control, which has no EME sequence (Table 7). The ocs enhancer (SEQ ID: 39) had the greatest increase in expression of the reporter gene in maize protoplasts. These results indicate that expression level can be modulated by modifying the size (length) of the EME.

TABLE 7

Effects on gene expression by truncated EME1 variants

| SEQ ID | Size | Mean | Significance grouping |
|---|---|---|---|
| 39 | 21 bp | 4.735 | A |
| 1 | 17 bp | 3.552 | B |
| 40 | 16 bp | 3.040 | C |
| 41 | 15 bp | 2.316 | D |
| 61 | 15 bp | 1.592 | E |
| 59 | 14 bp | 1.371 | F |
| 2 | 14 bp | 1.251 | G |
| 60 | 14 bp | 1.162 | H |
| 58 | 13 bp | 1.143 | H |
| 57 | 13 bp | 1.125 | Hi |
| 55 | 12 bp | 1.114 | Hi |
| 54 | 12 bp | 1.063 | I |
| 56 | 13 bp | 1.049 | I |
| 53 | 12 bp | 1.048 | I |
| Control | | 0.778 | J |

Example 6

Effects of Sequence Variations of Tested EMEs

Several sequence variations of EME2 were tested to determine sequence variation effects for modulating gene expression. Data for the 2×EME2 sequence variations designated SEQ ID NOS: 9-19 evaluated for the expression modulation of the CaMV35S minimal promoter are shown in Table 8.

TABLE 8

Sequence variations and EME expression modulation

| Activation element | SEQ ID NO for 1X EME | P Value | Fold Change relative to Control | Replicates |
|---|---|---|---|---|
| Control (CAMV35S min) - No EME | — | — | — | 5240 |
| 2X EME2 | 9 | <.0001 | 1.8459268 | 1220 |
| 2X EME2 | 10 | <.0001 | 1.585005903 | 928 |
| 2X EME2 | 11 | <.0001 | 2.556080283 | 1681 |
| 2X EME2 | 12 | <.0001 | 1.236127509 | 2830 |
| 2X EME2 | 13 | 0.0351 | 1.165879575 | 3005 |
| 2X EME2 | 14 | <.0001 | 1.828217237 | 1178 |
| 2X EME2 | 15 | <.0001 | 4.06729634 | 808 |
| 2X EME2 | 16 | <.0001 | 2.863046045 | 954 |
| 2X EME2 | 17 | <.0001 | 3.272333727 | 150 |
| 2X EME2 | 18 | <.0001 | 1.389413617 | 1147 |
| 2X EME2 | 19 | <.0001 | 1.494883904 | 1092 |

After testing different size variants of the EME2 sequence, a series of modifications in base position 7 and/or base position 8 (SEQ ID NO: 9-19) in the 14 bp EME2 sequence (SEQ ID NO: 5) were made. Some of these changes altered the nucleotides in these 2 positions while maintaining a palindromic sequence (SEQ ID NO: 12, SEQ ID NO: 18 and SEQ ID NO: 19). These sequence variants were tested as 2 copies of the variant EME2 upstream of the CaMV 35S minimal promoter in the previously described expression cassette with the reporter gene and sorghum GKAF terminator. In the maize protoplast assay, each of the EME sequence variants showed a significant increase in reporter gene fluorescence over the control as shown in Table 8. These results indicate sequence variants based on the EMEs demonstrated herein are useful to modulate gene expression levels.

The enhancer (SEQ ID NO:30) was used to create a new set of 7 variants in which two bases were systematically altered while maintaining the palindromic sequence (SEQ ID NO:20-29). These variations are referred as "V" series. For example, base 1 was changed from "A" to "G;" consequently, base 16 was changed from "T" to "C" to maintain the palindromic sequence (SEQ ID NO: 20) resulting in a 15 bp version of EME2 (SEQ ID NO: 34). These variants were tested by inserting one copy of the variant at the −50 location of the TSS in the ZmGOS2 promoter in an expression cassette containing the Sorghum intron, a reporter gene (e.g. ZsGreen) and sorghum gamma kafarin (GKAF) terminator, and then expression levels were assayed in maize leaf protoplasts. None of the tested variants reached expression levels similar to EME2 (SEQ ID NO: 4) (Table 9); however they displayed varying expression levels. Two variants resulted in expression levels significantly higher than the control, which is the vector with no EME inserted in ZmGOS2 promoter. One of the variants was the one that created a 15 bp EME2 (SEQ ID NO: 20) while the other variant changed base 7 from "G" to "T" and base 10 from "C" to "A." (SEQ ID NO: 26). Changes to base 3 from "G" to "T" and base 14 from "C" to "A" (SEQ ID NO: 22) caused the expression level to be significantly lower than the control or other variants tested, including a random palindromic sequence (SEQ ID NO:27), which was included to evaluate whether inserting a palindromic sequence would have an effect. The changes in nucleotides that abolish increased expression levels observed for these EMEs provide insight on which bases may be critical in these elements for increasing expression levels.

TABLE 9

"V" series expression modulation series and their effect on expression levels in comparison to controls without those variations.

| SEQ ID NO: | Mean | Significance Grouping |
|---|---|---|
| 4 | 4.9095 | A |
| 20 | 3.4795 | B |
| 26 | 2.3140 | C |
| Control (no EME) | 1.5336 | D |
| 24 | 1.4248 | D |
| 25 | 1.3343 | E |
| 23 | 1.1590 | F |
| 29 | 1.1583 | F |
| 21 | 1.1313 | Fg |
| 27 | 1.1095 | Fg |
| 28 | 1.0659 | G |
| 22 | 0.9629 | H |

Example 7

Position Effects of Tested EMEs

Several configurations of the EMEs were tested to determine location/position effects for modulating gene expression. Data for EMEs designated as 1×EME2 and 4× EME1 are shown in Table 10 below.

TABLE 10

EMEs and effects on location with respect to the transcriptional start site

| EME | SEQ ID NO for 1X EME | Location in FIG. 1 | Activation element Location (relative to TSS) | Fold Change (relative to control) | Replicates |
|---|---|---|---|---|---|
| Control | | | No EME control | — | 11748 |
| 1X EME2 (14 bp) | 5 | 1 | −550 | 1.39 | 13655 |
| 1X EME2 (14 bp) | 5 | 2 | −50 (Original location) | 3.84 | 11566 |
| 1X EME2 (14 bp) | 5 | 3 | +75 (5'UTR) | 0.93 | 11394 |
| 1X EME2 (14 bp) | 5 | 4 | +196 (Within the Intron) | 1.15 | 10026 |
| 1X EME2 (14 bp) | 5 | 5 | +1170 | 1.23 | 9600 |
| 1X EME2 (14 bp) | 5 | 6 | +1901 (3'UTR) | 0.44 | 10151 |
| 1X EME2 (14 bp) | 5 | 7 | +2172 (Outside of the transcript; +100 of the terminator or 3'UTR) | 0.96 | 10796 |
| 4X EME1 | 1 | 1 | −550 | 1.28 | 11626 |
| 4X EME1 | 1 | 2 | −50 (Original location) | 2.55 | 10272 |
| 4X EME1 | 1 | 3 | +75 (5'UTR) | 0.37 | 10592 |
| 4X EME1 | 1 | 4 | +196 (Within the SB-Ubi Intron) | 0.67 | 9398 |
| 4X EME1 | 1 | 5 | +1170 (downstream of Intron) | 0.70 | 11616 |
| 4X EME1 | 1 | 6 | +1901 (3'UTR) | 0.55 | 10973 |

To determine whether EME1 or EME2 sequences (SEQ ID NO: 1 and SEQ ID NO: 4) can alter expression levels if these sequences are inserted in various locations relative to the TSS, a series of expression constructs were made as shown in FIG. 1. This expression cassette includes the ZmGOS2 promoter along with the sorghum UBI intron, a reporter gene and sorghum GKAF terminator. Up to seven different locations were tested with either 4 copies of EME1 (SEQ ID NO: 1) or 1 copy of EME2 (SEQ ID NO: 5): site 1: −520 upstream of TATA box, site 2: −20 upstream of TATA, site 3: 5' UTR upstream of sorghum UBI intron, site 4: insertion in sorghum UBI intron, site 5: 5' UTR downstream of sorghum UBI intron, site 6: insertion within the 3' UTR, and site 7: 3'UTR of sorghum GKAF terminator outside of the transcript. Each construct showed a significant change in reporter gene expression in maize protoplasts as shown in Table 10. When the EME1 sequence is inserted in the promoter region, the expression levels of the reporter gene are significantly increased while insertion in the other 5 locations within the expression cassette resulted in a significant decrease of the expression of the reporter gene. A significant increase in gene expression was observed when EME2 (SEQ ID NO: 5) was inserted in locations within the promoter, within sorghum intron or the 5' UTR region after the sorghum intron. However, a significant decrease in reporter gene expression was concluded when EME2 was inserted in the 5' UTR region before the sorghum intron or either location within the sorghum GKAF terminator. The location of either EME within the expression cassette helps gene expression modulation using these sequences.

Example 8

Gene Expression Modulation by EMEs in Transformed Maize Plants

Expression cassettes evaluated in maize protoplasts assays were validated in stably transformed maize plants. The appropriate constructs were made for *Agrobacterium*-mediated transformation of maize, resulting in random insertion of T-DNA within maize genome. Leaf samples were taken from T0 seedlings to determine copy number of different elements within the right border and left border of the T-DNA integrated within the plant genome. Only plants determined as single copy for these multiple elements were chosen for characterization. Another leaf sample was taken from each plant deemed as single copy events to determine expression levels of the reporter gene (e.g. ZsGreen) relative to a reference gene by qRTPCR. When 1-3 copies of EME2 (SEQ ID NO: 3) was cloned at −20 location upstream of the TATA box (or −50 relative to the TSS) in the ZmGOS2 promoter, a change in expression (2.3-25.8 median value vs. 0.47 for control, FIG. 2) was determined in T0 leaf when compared to the control vector with no EME2 sequence. Similar to what was observed in maize protoplasts, a single copy of EME2 was sufficient to increase expression of the reporter gene over the control, and additional copies of EME2 resulted in a higher expression level of the reporter gene than a single copy of EME2. EME1 was evaluated in a similar manner as described for EME2 in these T0 transgenic plants. When 1-4 copies of EME1 are present in the ZmGOS2 promoter, the relative gene expression value quantified increased over the value for the control vector (FIG. 3). Thus, consistent with the protoplast assays, these qRTPCR results demonstrated that EMEs can increase expression levels of a polynucleotide at a whole plant level where the recombinant DNA construct has been stably incorporated. This stably integrated gene expression modulation further supports the notion that modifying an endogenous genomic locus with site specific changes to create an EME or insert 1×, 2×, 3× or 4× copies of plant-derived EMEs as described herein would also be expected to modulate gene expression.

T1 plants for these constructs except 1 copy of EME1 were grown to confirm the result obtained in the T0 experiment. In this experiment, up to 16 plants for each event with two to three events planted per construct were grown and evaluated in a greenhouse. In addition to the different number of EME copies and no EME control, transgenic plants containing maize ubiquitin (UBI) promoter with the maize ubiquitin intron driving the reporter gene (e.g. ZsGreen) were included as a positive control because this promoter is well-characterized, and its expression level is considered high in both root and leaf tissues that were evaluated. Maize GOS2 promoter is about 25% the strength in terms of expression level to maize UBI promoter. Leaf tissue was sampled at three different developmental stages: V6, V8 and V12 while a root sample was only taken at V12. For leaf samples both mRNA and protein expression were evaluated for the reporter gene while only mRNA expression was evaluated for the reporter gene in root samples. The mRNA and protein data for leaf samples are positively correlated for all three developmental stages, and that the correlation is statistically significant at p<0.0001 (Pearson Linear Correlation). For V6, V8 and V12 stage, plants with constructs containing 1× to 3×EME2 demonstrated significantly increased expression in the leaf when compared with the maize GOS2 promoter control containing no EME sequence (FIG. 5). When either 2× or 3×EME2 are inserted into the maize GOS2 promoter, expression levels are significantly greater that the expression levels achieved by the maize ubiquitin promoter (Table 11). However, plants containing 2× to 4×EME1 did not exhibit expression of reporter gene at a level as much as EME2 in the leaf. Plants containing 2× to 4× copies EME1 showed a significant increase in expression in V6 leaf tissue. Other than V6 stage, expression levels in the leaf of plants containing 2× to 4× copies of EME1 did not result in higher expression levels. EME1 has a greater effect on expression in root tissue than leaf tissue (FIG. 6). In root tissue, 2× to 4× copies of EME1 and 1× to 3× copies of EME2 inserted in maize GOS2 promoter as previously described significantly increased reporter gene expression (Table 12). In another variation, 2× or 3× copies of EME2 increased the expression strength of the maize GOS2 promoter to levels significantly higher than expression levels achieved by maize UBI promoter with the maize UBI intron. Further, the mRNA and protein data were positively correlated for all three developmental stages, and that this correlation is statistically significant at p<0.0001.

TABLE 11

ZsGreen expression levels in leaf tissue at V12 stage in T1 plants

| Promoter | SEQ ID | Class | Mean | Std Error | Significance grouping |
|---|---|---|---|---|---|
| ZmGOS2 | 17 | 2X EME1 | 1.102935 | 0.097712 | BCDE |
| ZmGOS2 |  | None | 1.134665 | 0.115127 | BCDE |
| ZmGOS2 | 17 | 4X EME1 | 1.235011 | 0.101415 | CDE |
| ZmGOS2 | 17 | 3X EME1 | 1.474279 | 0.122854 | EF |
| ZmGZOS2 | 4 | 1X EME2 | 2.753511 | 0.223194 | H |
| UBIZM |  | None | 4.283125 | 0.413672 | IJK |
| ZmGOS2 | 4 | 2X EME2 | 6.730328 | 0.571054 | LM |
| ZmGOS2 | 4 | 3X EME2 | 12.2902 | 1.010799 | P |

TABLE 12

ZsGreen expression levels in root tissue at V12 stage in T1 plants

| Promoter | SEQ ID | Class | Mean | Std Error | Significance grouping |
|---|---|---|---|---|---|
| ZmGOS2 |   | None | 0.59391 | 0.06064575 | A |
| ZmGOS2 | 17 | 2X EME1 | 1.865621 | 0.16348927 | G |
| ZmGOS2 | 17 | 3X EME1 | 3.899812 | 0.31254956 | IJ |
| ZmGOS2 | 4 | 1X EME2 | 4.054389 | 0.31873811 | IJ |
| ZmGOS2 | 17 | 4X EME1 | 4.422228 | 0.35361067 | IJK |
| UBIZM |   | None | 4.879029 | 0.45500717 | JK |
| ZmGOS2 | 4 | 2X EME2 | 7.622568 | 0.63069706 | LMN |
| ZmGOS2 | 4 | 3X EME2 | 9.412221 | 0.74899065 | NO |

Six different locations were tested with 4 copies of EME1 (SEQ ID NO: 1) in T0 transgenic plants: site 1: −550 upstream of TSS, site 2: −50 upstream of TSS, site 3: 5' UTR before sorghum UBI intron, site 4: insertion in sorghum UBI intron, site 5: 5' UTR after sorghum UBI intron and site 6: insertion within transcript of 3' UTR. Leaf samples from plants determined to contain a single copy of the appropriate expression cassette were evaluated using qRTPCR. Similar to the protoplast data, the highest expression was assessed when the 4×EME1 was inserted at site 2 in the ZmGOS2 promoter (FIG. 4), resulting in the median value to increase from 0.47 for no EME control to 3.56. Thus, consistent with the protoplast assays, these qRTPCR results demonstrated that EMEs can increase expression levels of a polynucleotide at a plant level.

Example 9

Endogenous Gene Expression Modification Through Genome Editing

In an embodiment, the regulatory elements set forth in SEQ ID NOS: 1-68 or fragments thereof or variants thereof, and compositions comprising said sequences, can be inserted in operable linkage with an endogenous gene by genome editing using a double-stranded break inducing agent, such as a guided Cas9 endonuclease. Based on the availability of the genetic loci sequence information guide RNAs are designed to target a particular endogenous gene. For example, maize genes involved in improving agronomic characteristics of a maize plant are suitable targets.

In an embodiment, specific point mutations, insertions or deletions of the regulatory elements set forth in SEQ ID NOS: 1-68 or fragments thereof or variants thereof, are made in an endogenous polynucleotide in a site specific manner to introduce or removed expression modulation elements described herein. For example, 4-5 point mutations can recreate SEQ ID NO: 1 in an endogenous gene that is involved in yield increase or drought tolerance by genome editing using a double-stranded break inducing agent, such as a guided Cas9 endonuclease. Based on the availability of the genetic loci sequence information guide RNAs are designed to target a particular endogenous gene.

Guided Cas9 endonucleases are derived from CRISPR loci (Clustered Regularly Interspaced Short Palindromic Repeats) (also known as SPIDRs-SPacer Interspersed Direct Repeats) which are a family of recently described DNA loci. CRISPR loci are characterized by short and highly conserved DNA repeats (typically 24 to 40 bp, repeated from 1 to 140 times—also referred to as CRISPR-repeats) which are partially palindromic.

Cas endonuclease relates to a Cas protein encoded by a Cas gene, wherein the Cas protein is capable of introducing a double strand break into a DNA target sequence. The Cas endonuclease is guided by a guide polynucleotide to recognize and optionally introduce a double strand break at a specific target site into the genome of a cell (U.S. Application Publication No. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

In one embodiment, the methods comprise modifying the expression of an endogenous gene in a cell by introducing the regulatory elements herein in operable linkage with an endogenous gene. The regulatory elements can be introduced in operable linkage to an endogenous gene using any genome editing technique, including, but not limited to use of a double-stranded break inducing agent, such as guided Cas9/CRISPR system, Zinc finger nucleases, TALENs. See Ma et al (2014), *Scientific Reports*, 4: 4489; Daimon et al (2013), *Development, Growth, and Differentiation*, 56(1): 14-25; and Eggleston et al (2001) BMC Genetics, 2:11.

Example 10

Promoter Deletion Experiments for Endogenous Gene Expression Modulation

One of the standard methods for identifying motifs controlling the characteristics of a promoter's expression capabilities involves creating a truncation or deletion series of sequences driving a reporter gene marker such as GUS, GFP, luciferase, or any other suitable fluorescent protein. One typical approach begins with a deletion series removing ~10 percent of the promoter sequence beginning at the 5' end. Expression of the marker gene for each truncation is quantified and observations made regarding changes in expression levels. Once a distinction has been made between truncations that have no effect and those that do, a deletion series can be made to further tease out which precise sequences have an impact on expression levels.

For example, if a 2 kb promoter sequence is the initial starting sequence, sequences with lengths of 2 kb–1 kb show some the same level of expression, it is generally expected that no significant motifs affecting expression in the tissue tested are present in the most 5' 1 kb of sequence. If it is found that truncations under 0.4 kb lose all function, it is determined that the minimal promoter for expression is about 0.4 kb. Then, a deletion series is created where a 100 bp region is sequentially removed, from within the remaining 1 kb, in a stepwise fashion until a deletion series is created where each region of the remaining 1 KB sequence, upstream of the "minimal promoter" has been removed for testing. Thus, for example, 5 new deletion series all with a length of about 0.9 kb (0.4 kb of minimal promoter+0.5 kb of upstream region) are constructed for testing in the same fashion as before.

These deletion series can be tested through stable transformation of a suitable plant, through transient expression analysis, or in isolated protoplasts.

Example 11

Gene Expression Modulation by EMEs in Dicot Plants

A T-DNA based binary construct was created, containing 1 to 3 copies of EME1 (SEQ ID NO: 17) or EME2 (SEQ ID NO: 4) upstream of a minimal CaMV 35S minimal promoter driving expression of a reporter gene such as beta-glucoronidase, which is commonly referred as GUS. In addition to the constructs containing the EME sequences, two control constructs were also transformed. One construct has only the minimal promoter driving the reporter gene, e.g., GUS. The expectation is that no reporter gene expression would be observed when the tissue is processed. The other construct acts as a positive control since it contains the CaMV 35S promoter with its enhancer sequences driving the reporter gene. The expectation is that reporter gene expression would be observed in both leaf and root tissue of young seedlings. *Arabidopsis* plants were transformed using *Agrobacterium*, and then positive transformants were selected using an herbicide. Transgenic seedlings were processed to evaluate expression of the reporter gene, GUS. As expected, the plants containing the minimal CaMV 35S promoter showed no GUS expression while the positive control plants showed blue staining in both root and leaf tissue. Transgenic plants containing 1 to 3 copies of EME1 upstream of the CaMV 35S minimal promoter primarily exhibited GUS expression in root tissue. Some GUS expression was also observed near edge of leaf tissue in plants containing the constructs with 2 or 3 copies of EME1. The strongest reporter gene expression was observed when 3 copies of EME2 were present upstream of the minimal promoter. The GUS staining pattern was observed in both root and leaf tissue and visually appeared similar to the noticed pattern for the positive control. Thus, both EME1 and EME2 increase gene expression in dicot plants.

In addition to *Arabidopsis*, these constructs containing 1 to 3 copies of EME2 upstream of the minimal CaMV 35S promoter were evaluated in isolated soybean tissue. Similar to *Arabidopsis*, protein expression was detected when 2× or 3×EME2 were present upstream of this minimal promoter. In addition to the CaMV 35S minimal promoter, 1× to 3×EME2 were introduced into a soybean promoter by changing nucleotides to recreate EME2 sequence (SEQ ID NO: 4) with the native promoter sequence separating the EMEs when multiple copies of EME2 were present. An increase in protein expression was detected in tissue with constructs containing EME2. Another construct was made that had two copies of EME2 without any additional bases between the two copies. One copy had SEQ ID NO: 33, and the other copy had SEQ ID NO: 4. This combination of sequences was inserted approximately −50 upstream of TSS and resulted in the highest increase in protein expression as tested in this assay. Thus, nucleotides separating multiple copies of EME2 is not necessary to modify gene expression in plant cells using EMEs described herein.

What is claimed is:

1. A method of modulating expression of an endogenous polynucleotide in a plant cell, the method comprising altering one or more nucleotides in a regulatory region of the endogenous polynucleotide such that the regulatory region of the polynucleotide comprises an expression modulating element having at least one copy of a polynucleotide sequence selected from the group consisting of SEQ ID NOS: 1, 2, 40 and 41.

2. The method of claim 1, wherein the alteration of one or more nucleotides is by genome modification.

3. The method of claim 1, wherein the expression modulation element is present within about 10 to about 5000 bp from a transcriptional start site of the endogenous polynucleotide.

4. The method of claim 1, wherein the expression modulation element further comprises additional copies of the expression modulating element such that about 2× to 10× copies of the expression modulating elements are present in the regulatory region of the endogenous polynucleotide.

5. The method of claim 4, wherein the additional copies of the expression modulating element are present in one or more of the configurations selected from the group consisting of: head to head, head to tail, tail to head, tail to tail, and a combination thereof.

6. The method of claim 4, wherein the additional copies are separated by a spacer sequence.

7. The method of claim 1, wherein the expression modulating element is plant-derived and is heterologous to the endogenous polynucleotide.

8. The method of claim 4, wherein the additional copies of the expression modulating element is created by altering no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 27, 38, 39 or 40 nucleotides in the regulatory region of the endogenous polynucleotide.

9. The method of claim 1, wherein the expression modulating element is located upstream of the transcriptional start site of the endogenous polynucleotide.

10. The method of claim 1, wherein the expression of the endogenous polynucleotide is increased in the plant cell compared to a control plant cell not comprising the expression modulation element operably linked to the endogenous polynucleotide.

11. The method of claim 1, wherein the plant cell is maize, rice, soybean, sunflower, wheat, canola or sorghum.

12. The method of claim 1, wherein the endogenous polynucleotide is involved in drought tolerance, disease resistance, herbicide tolerance, pest resistance, yield increase, yield stability, nitrogen utilization efficiency or a combination thereof.

13. The method of claim 2, wherein the genome modification is (a) a site-specific double strand break (DSB) mediated by a polynucleotide-guided endonuclease, zinc finger nuclease, a transcription activator-like effector nuclease (TALEN), polynucleotide-guided recombinase or engineered site-specific meganucleases, or Argonaute or (b) a site-specific base edit mediated by an C•G to T•A or a A•T to G•C base editing deaminase enzymes.

14. The method of claim 1, wherein the expression modulating element is operably linked to a heterologous minimal core promoter.

* * * * *